United States Patent
Griffin et al.

(10) Patent No.: US 10,092,356 B2
(45) Date of Patent: Oct. 9, 2018

(54) RADIAL EMISSIONS FROM OPTICAL FIBERS

(71) Applicant: InnovaQuartz LLC, Pheonix, AZ (US)

(72) Inventors: Stephen E. Griffin, Peoria, AZ (US); Stuart F. Watson, Mesa, AZ (US)

(73) Assignee: InnovaQuartz LLC, Pheonix, AZ (US)

( * ) Notice: Subject to any disclaimer, the term of this patent is extended or adjusted under 35 U.S.C. 154(b) by 0 days.

(21) Appl. No.: 14/944,266

(22) Filed: Nov. 18, 2015

(65) Prior Publication Data

US 2017/0135765 A1   May 18, 2017

(51) Int. Cl.

| | |
|---|---|
| *G02B 6/26* | (2006.01) |
| *G02B 6/32* | (2006.01) |
| *G02B 6/38* | (2006.01) |
| *G02B 6/36* | (2006.01) |
| *A61B 18/22* | (2006.01) |
| *F21V 8/00* | (2006.01) |
| *A61N 5/06* | (2006.01) |
| *A61N 5/067* | (2006.01) |
| *A61B 18/00* | (2006.01) |

(52) U.S. Cl.
CPC ............ *A61B 18/22* (2013.01); *A61N 5/0601* (2013.01); *A61N 5/062* (2013.01); *G02B 6/0003* (2013.01); *G02B 6/262* (2013.01); *A61B 2018/00404* (2013.01); *A61B 2018/00577* (2013.01); *A61B 2018/2222* (2013.01); *A61B 2018/2244* (2013.01); *A61B 2018/2261* (2013.01); *A61B 2018/2266* (2013.01); *A61N 2005/063* (2013.01); *A61N 2005/067* (2013.01)

(58) Field of Classification Search
CPC .......... G02B 6/32; G02B 6/262; G02B 6/005; G02B 6/0028; G02B 6/003; G02B 6/0033; A61B 18/22; A61B 2018/2272; A61B 18/24; A61B 18/201; A61B 18/202; A61B 2018/2255; A61B 2018/2266
USPC .......... 385/29, 31, 33, 36, 38, 68, 74, 79, 84
See application file for complete search history.

(56) References Cited

U.S. PATENT DOCUMENTS

| | | |
|---|---|---|
| 4,669,467 A | 6/1987 | Willett et al. |
| 4,672,961 A | 6/1987 | Davies |
| 4,718,417 A | 1/1988 | Kittrell et al. |
| 4,732,448 A | 3/1988 | Goldenberg |
| 4,740,047 A | 4/1988 | Abe et al. |
| 4,842,390 A | 6/1989 | Sottini et al. |
| 4,967,745 A | 11/1990 | Hayes et al. |

(Continued)

*Primary Examiner* — Kaveh C Kianni
*Assistant Examiner* — Hung Lam
(74) *Attorney, Agent, or Firm* — Jonathan Goodman

(57) ABSTRACT

Radial emission optical fiber terminations that include conical elements can prevent axial emission and redirect all incident light to radial positions. One termination includes an optical fiber having an up-tapered terminus, the up-tapered terminus having a maximum taper diameter of at least 1.5 times the core diameter and ending at a cone-tip which has an apex angle in a range of about 70° to about 100°. Another termination includes a fiber cap that is a unitary construction of a glass tube and an optical element that bisects the glass tube. The glass tube includes an open end adapted to receive an optical fiber and a closed end. The optical element, consisting of fused quartz or fused silica, has an input face proximal to the open end of the glass tube and a conical face proximal to the closed end of the glass tube.

16 Claims, 14 Drawing Sheets

(56) References Cited

U.S. PATENT DOCUMENTS

| | | | |
|---|---|---|---|
| 5,001,737 A * | 3/1991 | Lewis | G21K 1/02 378/145 |
| 5,019,075 A | 5/1991 | Spears et al. | |
| 5,061,265 A | 10/1991 | Abela et al. | |
| 5,074,632 A | 12/1991 | Potter | |
| 5,093,877 A | 3/1992 | Aita et al. | |
| 5,104,392 A | 4/1992 | Kittrell et al. | |
| 5,106,387 A | 4/1992 | Kittrell et al. | |
| 5,125,404 A | 6/1992 | Kittrell et al. | |
| 5,192,278 A | 3/1993 | Hayes et al. | |
| 5,199,431 A | 4/1993 | Kittrell et al. | |
| 5,231,684 A | 7/1993 | Narciso et al. | |
| 5,242,438 A | 9/1993 | Saadatmanesh et al. | |
| 5,269,777 A | 12/1993 | Doiron et al. | |
| 5,290,275 A | 3/1994 | Kittrell et al. | |
| 5,292,320 A | 3/1994 | Brown et al. | |
| 5,342,355 A | 8/1994 | Long | |
| 5,343,543 A | 8/1994 | Novak et al. | |
| 5,354,294 A | 10/1994 | Chou | |
| 5,428,699 A | 6/1995 | Pon | |
| 5,468,239 A | 11/1995 | Tanner et al. | |
| 5,486,171 A | 1/1996 | Chou | |
| 5,495,541 A | 2/1996 | Murray et al. | |
| 5,496,307 A | 3/1996 | Daikuzono | |
| 5,496,308 A | 3/1996 | Brown et al. | |
| 5,498,260 A | 3/1996 | Rink et al. | |
| 5,509,917 A | 4/1996 | Cecchetti et al. | |
| 5,512,078 A | 4/1996 | Griffin | |
| 5,530,780 A | 6/1996 | Ohsawa | |
| 5,537,499 A * | 7/1996 | Brekke | A61B 18/24 385/123 |
| 5,562,657 A | 10/1996 | Griffin | |
| 5,571,099 A * | 11/1996 | Purcell, Jr. | A61B 18/24 606/17 |
| 5,695,583 A | 12/1997 | Bergh et al. | |
| 5,737,472 A | 4/1998 | Bernasson et al. | |
| 5,807,390 A | 9/1998 | Fuller et al. | |
| 5,824,005 A | 10/1998 | Motamedi et al. | |
| 5,908,415 A | 6/1999 | Sinofsky | |
| 6,102,905 A | 8/2000 | Baxter et al. | |
| 6,113,589 A | 9/2000 | Levy et al. | |
| 6,246,817 B1 | 6/2001 | Griffin | |
| 6,270,492 B1 | 8/2001 | Sinofsky | |
| 6,284,085 B1 | 9/2001 | Gwo | |
| 6,398,777 B1 | 6/2002 | Navarro et al. | |
| 6,398,778 B1 | 6/2002 | Gu et al. | |
| 6,522,806 B1 | 2/2003 | James et al. | |
| 6,687,436 B2 | 2/2004 | Griffin | |
| 6,712,526 B1 | 3/2004 | Fleenor | |
| 6,829,411 B2 | 12/2004 | Easley | |
| 6,893,432 B2 | 5/2005 | Intintoli et al. | |
| 6,986,764 B2 | 1/2006 | Davenport et al. | |
| 7,270,656 B2 | 9/2007 | Gowda et al. | |
| 7,273,478 B2 | 9/2007 | Appling et al. | |
| 7,386,203 B2 | 6/2008 | Maitland et al. | |
| 7,463,801 B2 | 12/2008 | Brekke et al. | |
| 7,524,316 B2 | 4/2009 | Hennings et al. | |
| 7,909,817 B2 | 3/2011 | Griffin et al. | |
| 8,073,297 B2 | 12/2011 | Griffin | |
| 8,211,095 B2 | 7/2012 | Gowda et al. | |
| 8,257,347 B2 | 9/2012 | Neuberger | |
| 8,285,097 B2 | 10/2012 | Griffin | |
| 8,435,235 B2 | 5/2013 | Stevens et al. | |
| 8,851,080 B2 | 10/2014 | Gowda et al. | |
| 9,488,782 B2 * | 11/2016 | Griffin | G02B 6/262 |
| 2002/0021869 A1 * | 2/2002 | Griffin | A61B 18/22 385/43 |
| 2005/0015123 A1 | 1/2005 | Paithankar | |
| 2005/0165279 A1 | 7/2005 | Adler et al. | |
| 2006/0104593 A1 * | 5/2006 | Gowda | G02B 6/262 385/140 |
| 2006/0282068 A1 * | 12/2006 | Griffin | A61B 18/22 606/13 |
| 2006/0291061 A1 | 12/2006 | Iyama et al. | |
| 2007/0106286 A1 | 5/2007 | Harschack et al. | |
| 2008/0287936 A1 | 11/2008 | Stinson et al. | |
| 2009/0240242 A1 | 9/2009 | Neuberger | |
| 2010/0135617 A1 | 6/2010 | Novak et al. | |
| 2010/0179525 A1 | 7/2010 | Neuberger | |
| 2011/0038580 A1 | 2/2011 | Griffin | |
| 2011/0282330 A1 | 11/2011 | Harschack et al. | |
| 2015/0057648 A1 | 2/2015 | Swift et al. | |

* cited by examiner

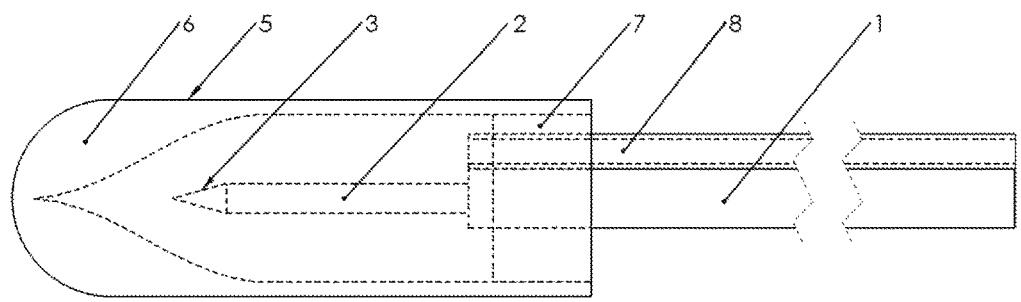
FIG. 1 (Prior Art, '390)
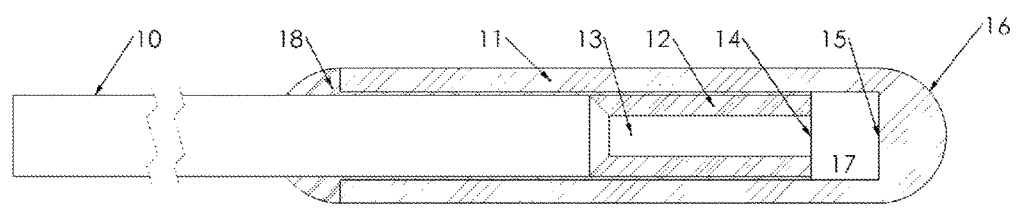
FIG. 2 (Prior Art, '877)
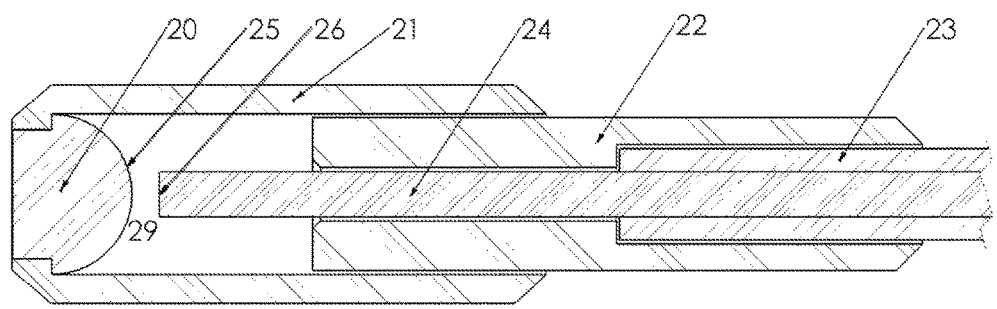
FIG. 3 (Prior Art, '684)

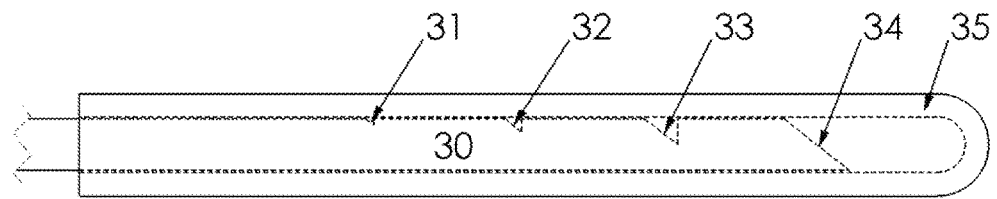
FIG. 4 (Prior Art, '320)
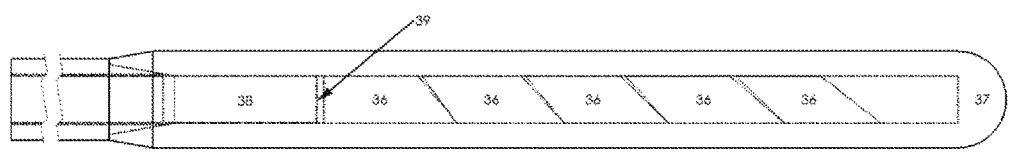
FIG. 5 (Prior Art, unpublished)
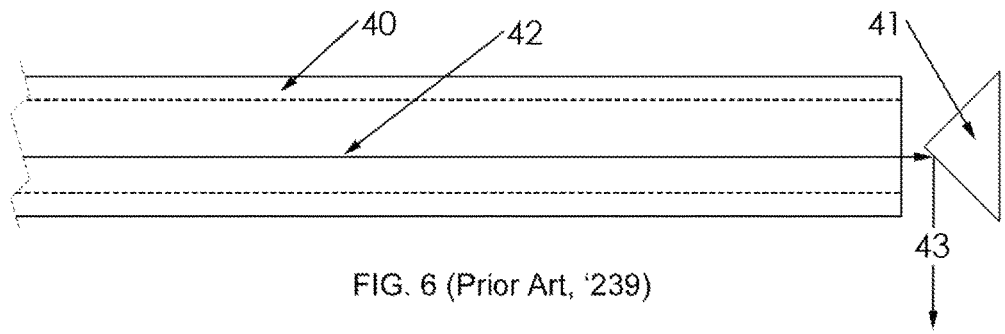
FIG. 6 (Prior Art, '239)

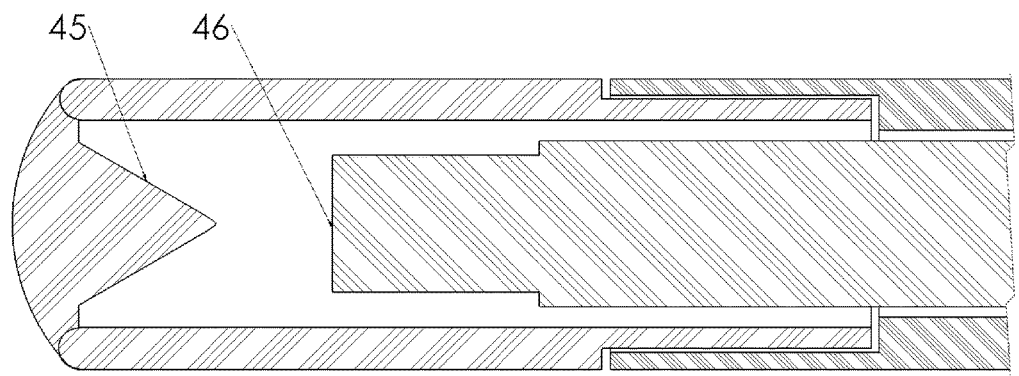
FIG. 7 (Prior Art, '235)
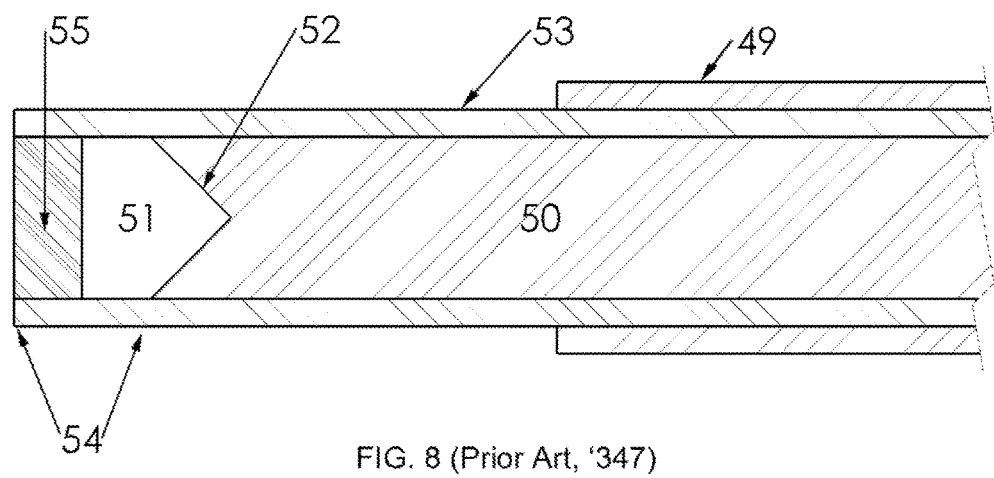
FIG. 8 (Prior Art, '347)

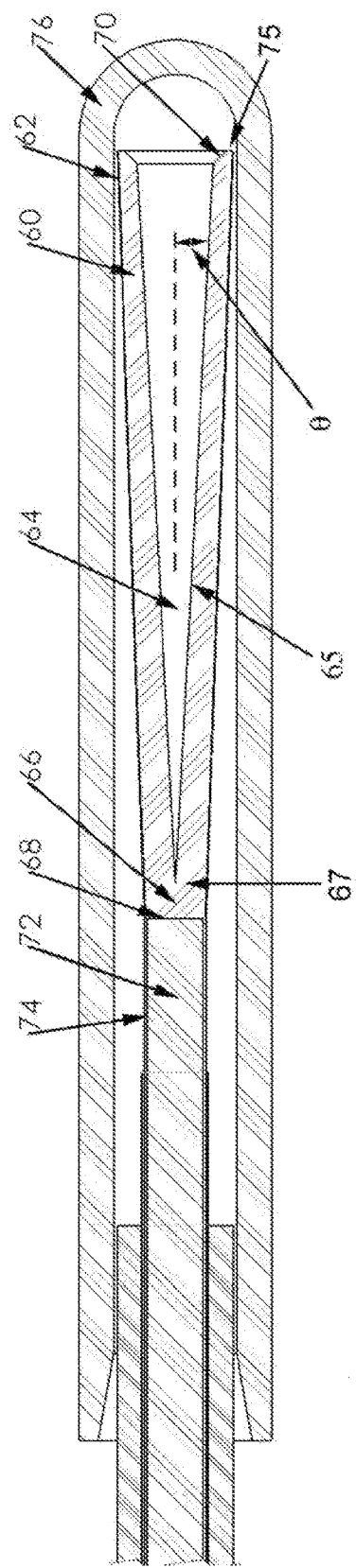
FIG. 9 (Prior Art, '097)

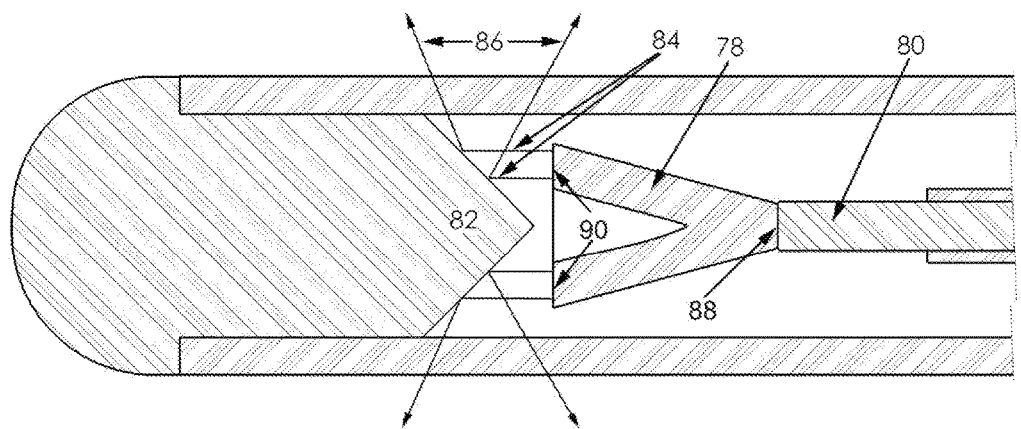
FIG. 10 (Prior Art, '438)
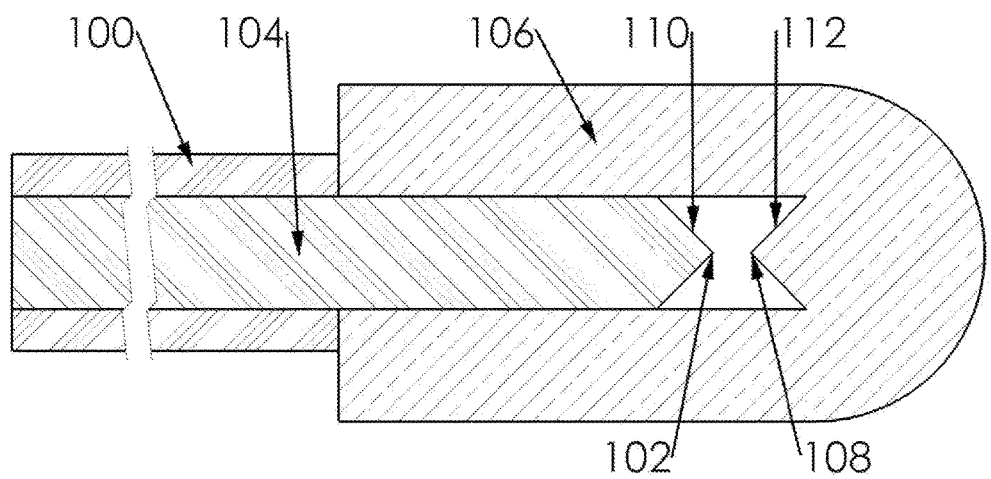
FIG. 11 (Prior Art, '242)

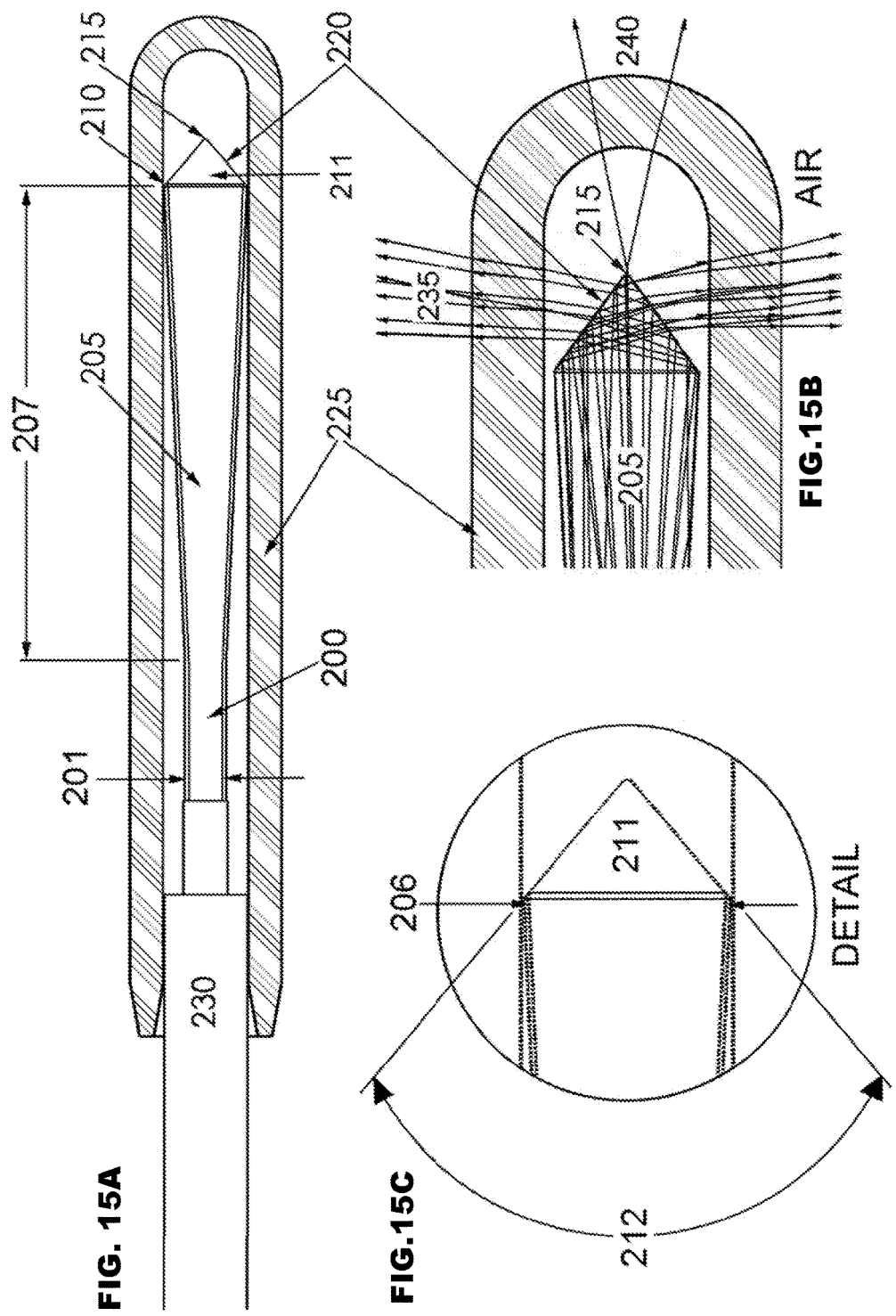

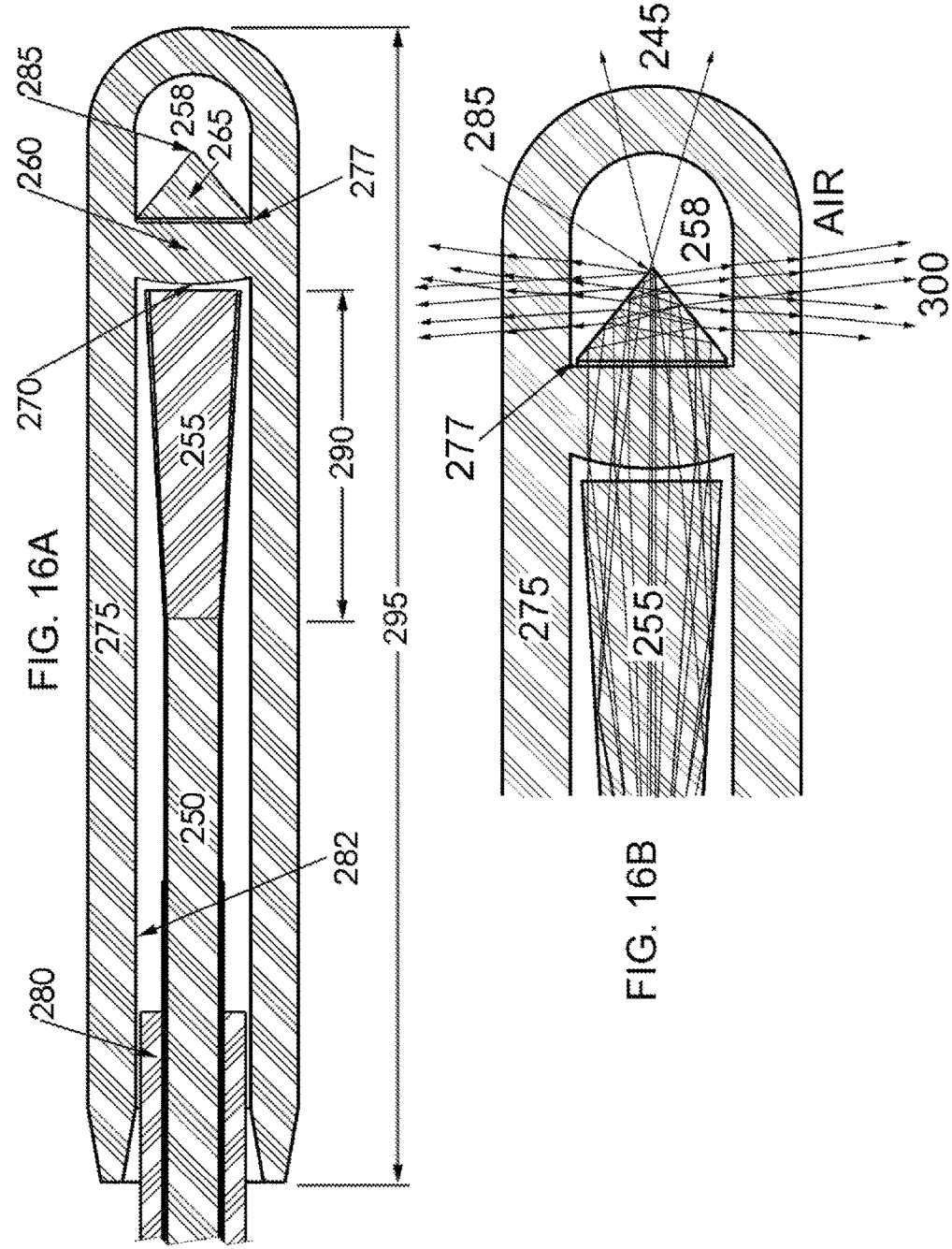

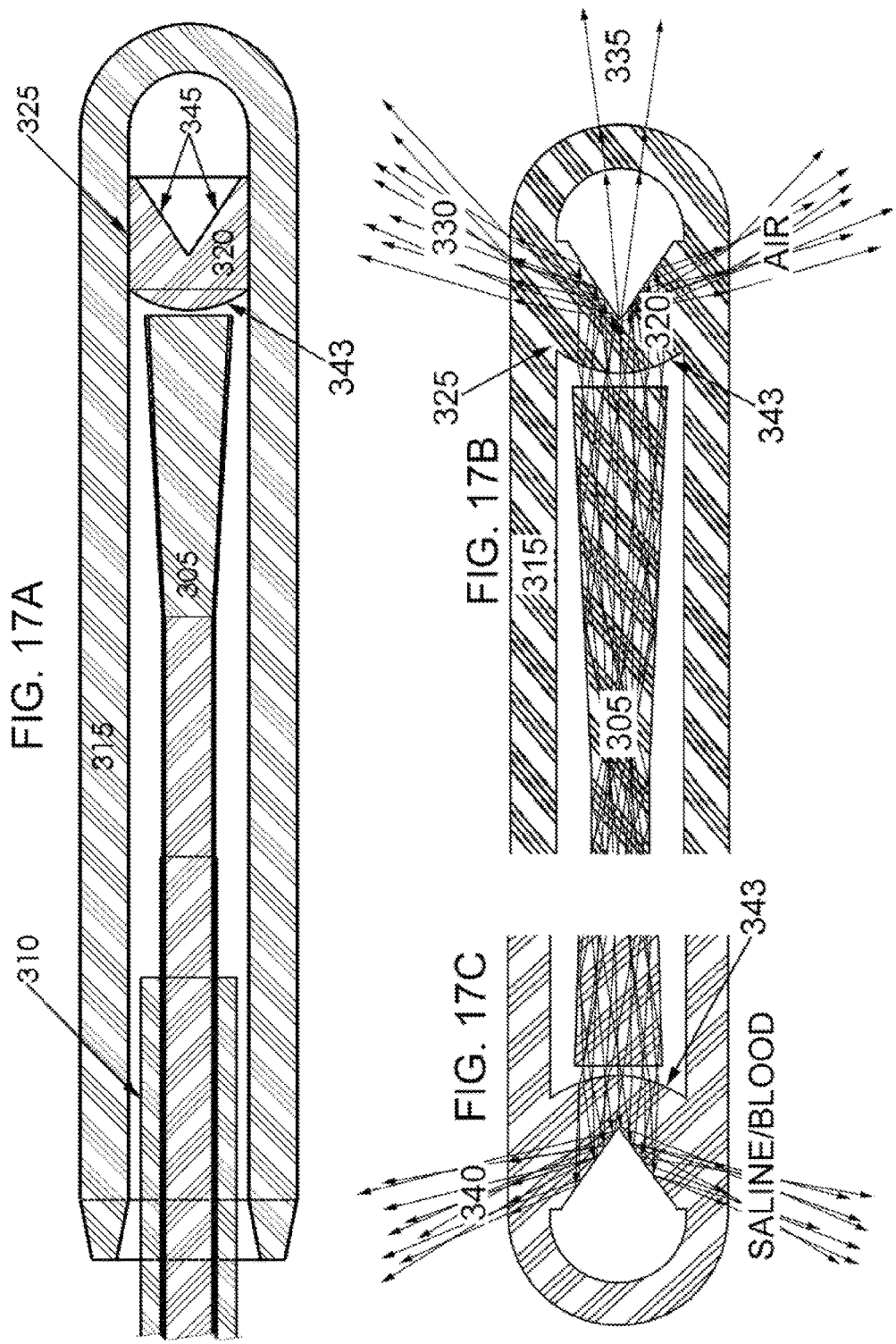

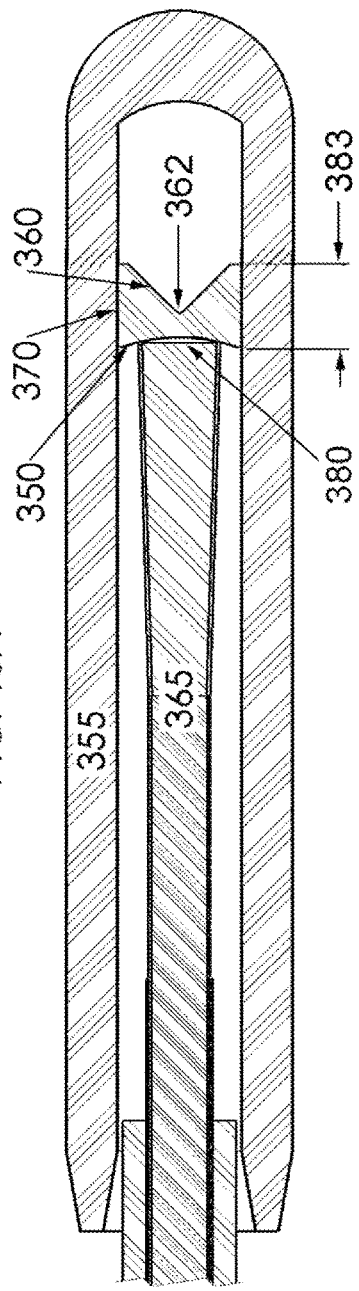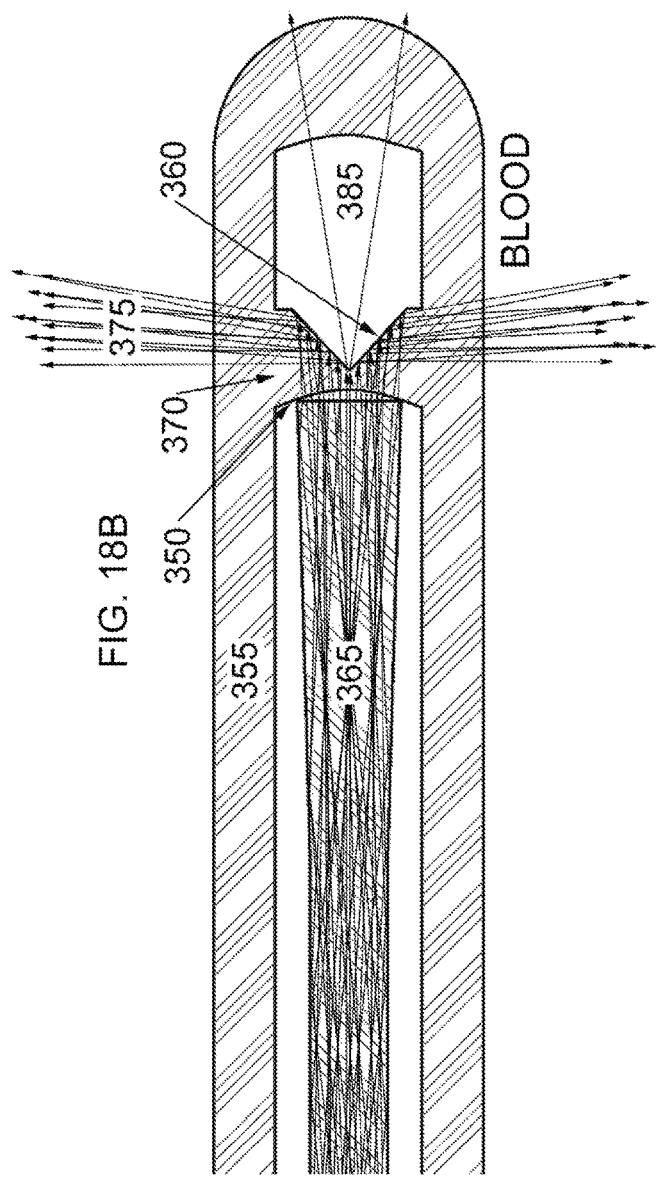

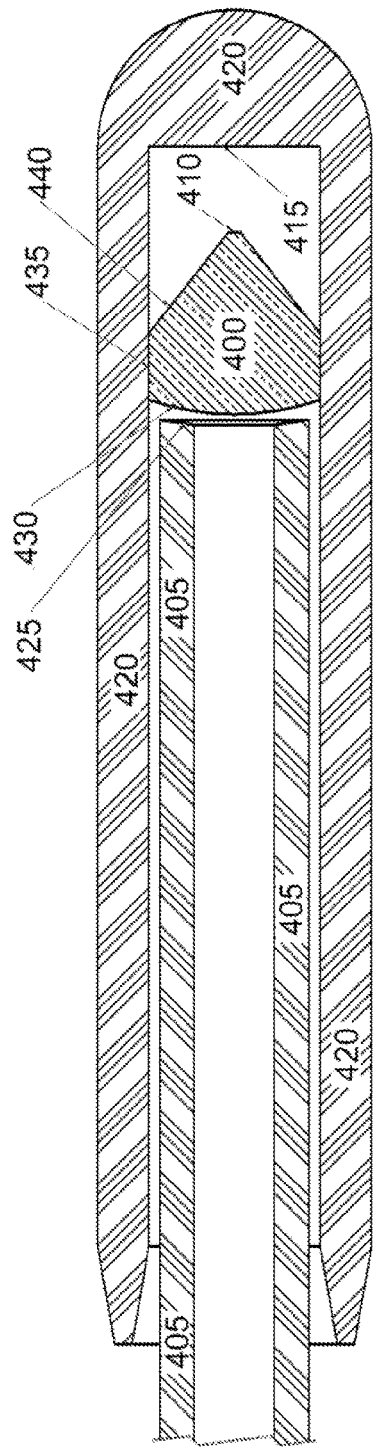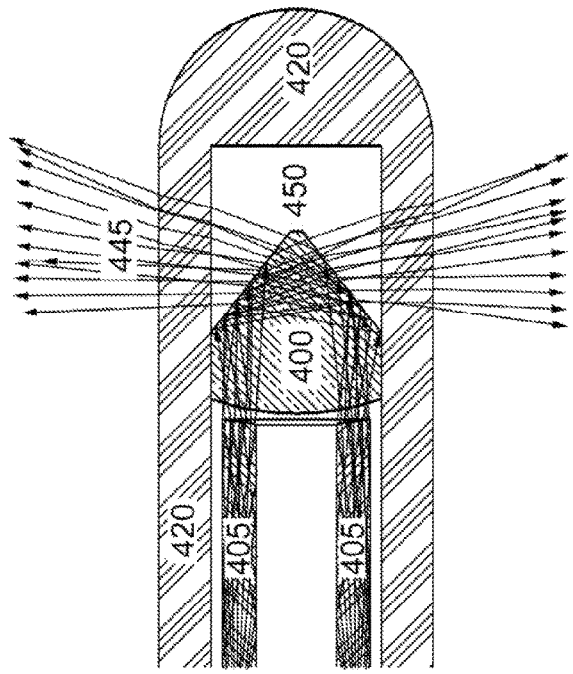
FIG. 19A
FIG. 19B

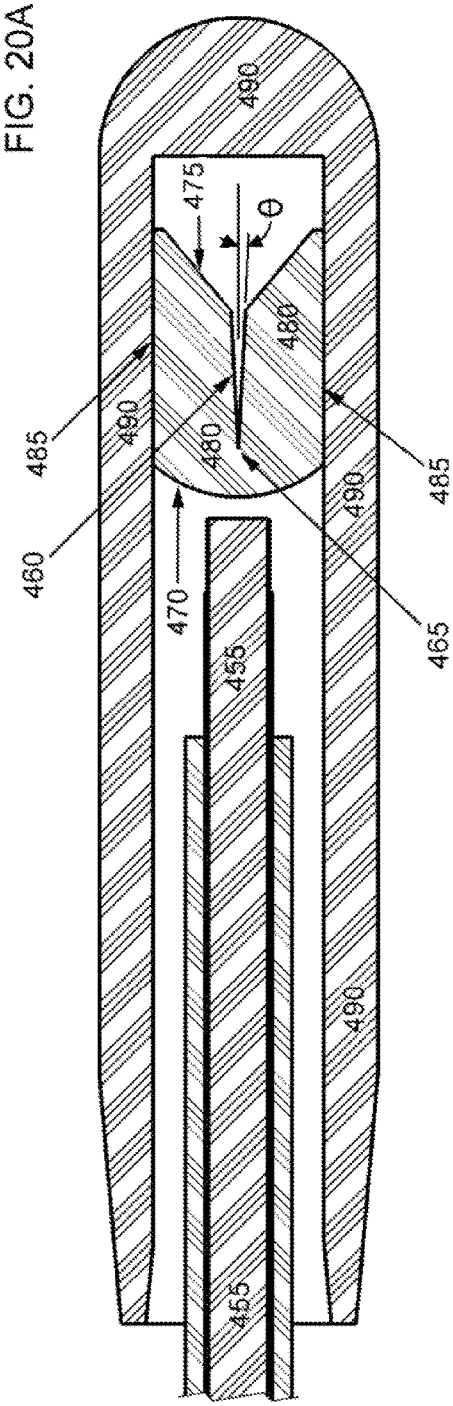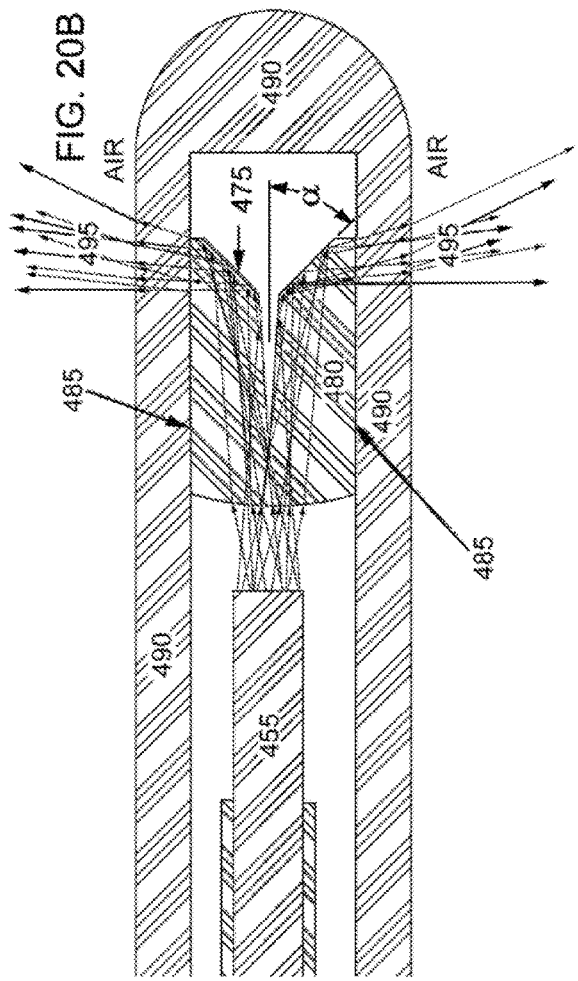

RADIAL EMISSIONS FROM OPTICAL FIBERS

FIELD OF THE INVENTION

This invention relates to fiber optic output profile modifications that are useful in the treatment of various intracorporeal disease states with intense light (e.g. lasers), particularly endovenous and peripheral artery diseases.

BACKGROUND

Lateral emission, radial emission, and diffusing output optical fibers are utilized in a variety of light-based surgical procedures including laser interstitial thermal therapy, endovenous laser ablation, endometrial coagulation and ablation, endovenous thermal therapy, and photodynamic therapy. Additional surgical interventions have been proposed using these modified output fibers including ablation, vaporization, and/or coagulation of tissue: including hyperplastic prostate tissue, laryngeal tumors, and atherosclerotic and vulnerable plaques.

Fiber modifications, including additions to optical fiber for altering the axial output, typically utilize scattering elements to produce diffuse energy emission over significant lengths of fiber (distal-termini) in both rigid and flexible designs. Fiber optics based upon scatter are generally very limited in total power handling capacity due to conversion of a significant portion of the photonic energy to thermal energy, and a reliance upon polymer matrices for carrying the scattering centers. These scattering modality outputs are referred, herein, as diffuse or diffusing output emissions.

"Radial emission" has been used to describe fiber output ranging from the standard divergence of a high numerical aperture (NA) and axial output (flat polished) optical fiber, to the reflected and refracted light from conical surfaces. Broadly defined, "radial output" fibers produce a radial component if the term "radial" includes any off-axis emission (i.e. any fiber output other than a truly collimated output has a "radial" component or components).

Alternatively, "lateral emitting" fibers are typically limited to single- and multi-point off axis emissions. One example of lateral emitting fibers includes fibers with a series of notches on one side (FIG. 4). Another example includes fibers launching into stacked angular segments of fiber where the angles differ and begin at a critical angle for just a portion of the angular modes within the delivery fiber and progress to the critical angle as calculated for all angular modes carried within the fiber (FIG. 5).

A difference in philosophy exists within the art of the broadest surgical application of such fiber technology: varicose vein surgery or endovenous laser treatment (ELT). Laser energy is used to selectively damage vessels for post-surgical absorption. One camp advocates indirect heating of veins (via heating the blood within the vein, often to boiling) by firing laser energy into the blood-filled vessel while moving the fiber along the length of the segment under treatment. If the fiber is maintained within the center of the vessel, the radiant output of the fiber is relatively uniform and the speed of movement of the fiber is adjusted such as to account to variations in vessel diameter and shape, this technique is said to minimize complications of overtreatment such as vascular perforation but it does result in considerable thrombosis (blood clotting). Such treatment is generally affected with a simple high numerical aperture (NA) and flat polished fiber with some provision for preventing fiber tip to vessel wall contact.

Another camp advocates heating the vessel wall directly and avoids interactions with the blood to prevent post-operative complications from excessive thrombosis. It is with the latter camp that uniform and true radial emission is most beneficial as vessel perforations are more likely to result from irregular application of laser energy.

Numerous examples of radial and lateral emitting fibers have been attempted, these include: U.S. Pat. No. 4,669,467 (Willett, et al.) teaches stress-induced mode mixing for adjusting the light spot size and spot overlap of a plurality of fibers, terminated within a transparent protective capsule where the individual fibers may be arranged such as to point in slightly different directions, for the treatment of vascular tissue or obstructions thereof. The reference cites studies from the early 1980s where direct contact between optical fibers delivering laser energy within blood vessels and resulted in thrombosis and vascular perforation. A series of related works—U.S. Pat. No. 4,718,417 (Kittrell, et al.), U.S. Pat. No. 5,104,392 (Kittrell, et al.), U.S. Pat. No. 5,106,387 (Kittrell, et al.), U.S. Pat. No. 5,125,404 (Kittrell, et al.), U.S. Pat. No. 5,199,431 (Kittrell, et al.), U.S. Pat. No. 5,290,275 (Kittrell, et al.), U.S. Pat. No. 4,967,745 (Hayes, et al.), U.S. Pat. No. 5,192,278 (Hayes, et al.)—teach additional utility including spectroscopic diagnostics, dosage control via feedback during surgery, and alternative constructions, including use of additional optical elements within the protective capsule for altered illumination and collection patterns: a lens, a mirror, a holographic element, a prism, different lenses for individual fibers or groups of fibers and an acousto-optic deflector.

U.S. Pat. No. 4,842,390 (Sottini, et al.) discloses a fiber optic device for angioplasty (FIG. 1) that utilizes a protective microcapsule 5 about the fiber output 3, where the capsule 5 is shaped 6 so as to produce a diverging annular output, or hollow cone, where the distribution of laser energy is further controlled by shaping the plastic clad fiber 1, in the illustrated case, as a cone tip 3. Sottini included a capillary 8 within the invention, providing communication between the cap interior volume, through the adhesive seal to the outside for the purpose of venting " . . . a dangerous pressure increase in the gas or air contained in the microcapsule" leading one to conclude that the efficiency of the radial emission was poor.

U.S. Pat. No. 5,093,877 (Aita, et al., FIG. 2) similarly teaches a protective cap 11 or capsule about a fiber 10 that serves as a beam conditioning 'microlens', where the closed end 16 of the transmissive capsule shapes the fiber output. Aita describes a gold or other radiopaque material ferrule 12 around the bare portion of the fiber 13, fixed in position with epoxy 18 and describes alternative curvatures for the first lens surface 15 and second lens surface 16 as well as filling the space 17 with materials of different refractive index for shaping the output from the flat fiber tip 14: one embodiment appearing virtually identical to '390 with a flat polished fiber. Filling the volume 17 with a fluid would produce a dangerous pressure increase, as described by Sottini, even at moderate laser powers unless the fluid were exceedingly transparent at the laser wavelength used and the device did not warm with use. Further, the ability of the second lens surface 16, or any optical surface in contact with whole or diluted blood, to refract the laser light emitted by the fiber tip 14 is greatly reduced because the refractive indices for whole blood ($\eta=1.38$) and dilute blood ($\eta=1.35$ @20%) are relatively similar to that of fused silica ($\eta=1.46$), particularly in comparison to air ($\eta=1.00$).

Similarly, U.S. Pat. No. 5,231,684 (Narciso, Jr., et al., FIG. 3) discloses a lens 20 mounted within the opening of the larger 21 of a pair of telescoping metal tubes 21 & 22 provided for redundant attachment to the optical fiber 23 buffer and cladding 24, where the space 29 between the lens curvature 25 and the fiber output 26 may be filled with fluid or elastomer having a similar refractive index as the fiber core and lens, thereby eliminating any refraction and therefore any function for the lens within the invention.

An abraded fiber core as a terminal diffusing segment of a surgical fiber is described in U.S. Pat. No. 5,019,075 (Spears, et. al.) teaches repair of physical damage to arterial walls during balloon angioplasty where light is intended to scatter in all directions along a length of the fiber that traverses the length of an angioplasty balloon along its axis.

U.S. Pat. No. 5,292,320 (Brown, et al.) teaches lateral delivery or side firing fibers (FIG. 4) where the single bevel tip 34 known to the art is augmented with a series of progressively shallower notches 33, 32 and 31 in the fiber 30, aligned substantially parallel to the primary bevel tip 34 plane, for redirecting fractions of the light within the fiber off the fiber axis and substantially in the same direction. Alternative embodiments include notches with differing angles as well as a spiral and other groove cut into a fiber for redirecting at least a portion of the energy carried therein. Brown teaches an optional protective cap 35 that is anything but optional. U.S. Pat. No. 5,496,308 (Brown, et al.) continues '320 where temperature dependent radiation form tissue is also collected in the device for monitoring and control.

An attempt to reduce Brown '320 to practice was made in 1994 by this inventor and Brown, but was promptly abandoned as impractical to manufacture and unsafe to use. An alternative design FIG. 5 was devised using angle polished segments of fiber 36, stacked within an elongated capsule 37 and butt-coupled to a flat polished 39 optical fiber 38 to produce a similar effect as sought in '320, but the distribution of the output energy profile proved difficult to control and the project was abandoned (non-patented work).

Similar to Aita '877, U.S. Pat. No. 5,342,355 (Long) teaches a transmissive cap for shaping the output of flat tip and convex tip optical fibers housed within the cap for heating tissue directly with laser light as refracted by the tip, heating the tip with laser light with the heat conducted to the tissue and exciting a gas trapped between the fiber output and the inside wall of the tip to form a plasma.

A system for treating prostate tissue with $CO_2$ lasers via urethral access (FIG. 6) was described in U.S. Pat. No. 5,468,239 (Tanner) wherein a hollow waveguide 40 delivers energy across a space to a reflective cone 41 which redirects the radiation in 360° radial to the cone and orthogonal 43 to the waveguide longitudinal axis along which rays 42 are exclusively drawn.

U.S. Pat. No. 5,737,472 (Beranasson, et al.) teaches control of radial emission from a segment of fiber through differential defect generation in the fiber diameter, for example as produced by controlled sandblasting.

U.S. Pat. No. 5,908,415 (Sinofsky) teaches a transparent, plastic tube which surrounds and extends beyond the distal end of a fiber, where the tube is filled with a silicone matrix containing light-scattering particles uniformly distributed therein. A reflective surface at the distal end of the tube serves to plug the tube such that light traveling from the fiber to the distal end of the tube is reinforced by the light that is reflected back from the reflective surface to produce a comparatively uniform light intensity along the length of the tube. Such devices have found utility in photodynamic therapy and other applications where low laser power is sufficient.

U.S. Pat. No. 6,398,777 (Navarro, et al.) teaches intraluminal contact between a fiber optic tip and a blood vessel wall, using laser energy from 200 μm to 1100 μm, but does also mention that the tip of the fiber may be rounded.

A method similar to Sinofsky '415, with elements of Brown '320 and its offspring echoed therein, is taught in U.S. Pat. No. 6,893,432 (Intintoli), where a tube affixed to the end of a fiber houses stacked segments of differential mixtures of transmissive and dispersive compounds providing successive bands of radial emission that may be tuned by altering the mixtures housed in the tube segments.

U.S. Pat. Nos. 7,270,656; 8,211,095; and 8,851,080 (Gowda, et al.) teach active cooling of diffusive fiber tips for laser interstitial thermal therapy where the tips are produced by "embedded scattering centers" and less than full 360° emission is controlled by "reflective means".

U.S. Pat. No. 7,273,478 (Appling) teaches away from radial emission for indirect heating of blood vessel walls via hot gas bubbles generated by axial output fibers, so long as those fiber tips are prevented from directly contacting the vessel wall by surrounding the fiber distal end with a ceramic spacer or, as described in U.S. Pat. No. 7,559,329 (Appling, et al.), an expandable spacer such as a wire basket.

U.S. Pat. No. 7,524,316 (Hennings, et al.) devotes a section to discussions of diffusing fiber tips stating therein, "The use of diffusing tip fibers for the treatment of varicose veins is unique and has not been previously described." '316 further teaches that shaped fiber tips are largely useless in direct contact with blood due to closely matching refractive indices essentially eliminating non-standard refractive output, and teaches the use of an internally threaded (diffusing) material screwed onto the fiber buffer as a diffuser, a ceramic or other scattering material in the form of a bead placed in the fiber output path within a transparent protective capsule housing both fiber and bead, and simply housing a cone-tipped fiber within a protective capsule and a rounded tip (orb) fiber with no protective capsule. Such capped cone tip fibers are in common use today.

U.S. Pat. Appl. Pub. No. 2005/0015123 (Paithankar) teaches the use of diffusing tip fibers produced by a polymer or ceramic "cover" that includes a scattering material in the form of a cylinder about a fiber tip or a ball on the fiber tip to, " . . . overcome the index of refraction matching properties of the optical fiber and the adjacent fluid or tissue."

U.S. Pat. No. 7,386,203 (Maitland, et al.) describes diffuser tip fibers in considerable detail and modifies the prior art by employing a shape memory polymer as the medium for carrying the scattering centers for diffusion, purportedly providing some control of that diffusion by way of the shape memory polymer substrate.

A transparent spacer/nozzle serving as a coaxial coolant conduit is taught in U.S. Pat. No. 8,435,235 (Stevens) where the delivery fiber is recessed within the transparent spacer such that radiation is emitted through the spacer wall, through the nozzle opening or both as delivered by an axial fiber or cone-tipped fiber. The transparent spacer is prevented from contacting vessel walls in manners similar to '329. '235 also teaches a version of '239 (FIG. 7) where radial emission is accomplished via reflection from an inverted cone 45 placed distal to the axial output fiber 46, various means of centering the fiber assembly within vessel walls, a fiber assembly with an absorbing or scattering material placed within a fiber output path, a shaped tip fiber with an internal lumen for fluid conduction, etc.

In U.S. Pat. No. 8,257,347 (Neuberger, FIG. 8) a radially distributed beam is described where reflections in all directions orthogonal to the fiber longitudinal axis is accomplished by removing a portion of the fiber buffer 49 to expose the cladding 53 and removal of part of the fiber core 50 producing a short, cladding only section 54 of fiber that terminates in a conical void 52 within the solid core 50. The hollow, cladding only section 54 is then plugging at the opening with a short quartz cylinder 55, preserving an air pocket 51 for the low refractive index such that light imparting the conical void in the core is redirected laterally, in all directions. As the drawing within '347 depicting this embodiment intimates (FIG. 5 surface 52, in the original drawing, is sketched as rough and ragged), producing such a structure with smooth and flat surfaces (a right circular cone as opposed to curved surface cones akin to a Hershey's Kiss) for efficient reflection is a challenging proposition and requires exceptionally thick cladding 53 (sketched as thicker than the fiber core in the original figure within '347); anything less than a highly polished surface at 52 will result in significant scatter and axial emission. Cladding is expensive, particularly when it is fluorine-doped silica, as it must be for '347 to be produced.

U.S. Pat. No. 8,285,097 (Griffin) describes a strategy similar to '347 that is also impractical for ELA (Endoluminal Laser Ablation) also known as ELT (Endovenous Laser Treatment), EVLT (EndoVenous Laser Therapy, Angiodynamics) and other, similar acronyms. As shown in FIG. 9, a glass clad 62 tube 60, or annular core fiber, is gently collapsed over the length of the tube until the inner diameter ceases to exist 66, thus forming a solid core to annular core fiber adapter. The open end of the annular fiber is chamfered 70 to redirect energy laterally while the solid end 66 is spliced 68 to the end of a clad 74, solid core fiber 72. The entire bare glass section is secured within a protective cap 76. Light from the solid core fiber is gently redirected into the annular core about the vanishing conical bore 64, encounters the critical angle chamfer 70 and exits as radial emission centered approximately at twice the chamfer angle. In one embodiment, near orthogonal performance may be obtained with divergence lower than the solid core fiber to which the solid to annular core adapter was fused but axial transmission remains problematic due to the chamfer 70 failing to extend completely across the annular core 75.

U.S. Pat. No. 5,242,438 (Saadatmanesh, et al.) discloses a device that " . . . includes special beam splitter or diverging device . . . a transmitting end portion which has a frusto-conical, annular configuration defining an annular end surface for emitting the laser radiation in a generally ring-like, cylindrical beam which is generally parallel to the longitudinal axis . . . " to avoid " . . . exposing the tip of the conical reflecting surface to the laser energy, and the surface can still function to reflect the radiation generally laterally of the axis . . . ". FIG. 10 illustrates this embodiment of the prior art where the "special beam splitter" 78 is analogous to the "solid core to annular adapter" in FIG. 9, but without the beam turning chamfer 70 at the terminal ID and instead relying upon the metallic reflector 82 distal to 78. It is of merit to note that the placement of the special beam splitter 78 between the fiber 80 output face 88 and the reflector 82 serves no real function other than the purported avoidance of exposing the tip of the conical reflecting surface 82 to the laser energy 84. As such, this embodiment serves only to permit imperfections in the reflecting cone and in the process generates Fresnel reflections within the device at 88 and 90.

Other embodiments in '438 are also directed to steering energy away from the center of terminal conical reflectors, including a concave conical pit in the fiber core akin to that in '347, produced with "a diamond drill" and a plurality of circumferentially disposed optical fibers or a ring output array. These strategies are necessary because directly illuminating a metallic conical reflector with the semi-Gaussian output profile of a laser driven optical fiber exposes the most difficult to prefect feature of the reflector, the cone point, to the highest energy densities. As with other prior art, overheating remains a central concern in '438 due to the inefficiencies of methods used for redirecting light therein.

U.S. Pat. No. 6,102,905 (Baxter, et al.) teaches a variety of embodiments of low power photodynamic therapy devices, similar to those taught by Sinofsky in '415, that must be low power due to the low temperature liability of the "optical elements" identified therein, include gradient index lenses, such as GRIN lenses (SELFOC®) produced by NSG America, made of gradient doped (germanium) silica, "cylindrical disks" and "hemispherical domes" made of PTFE, ETFE, FEP and PFA fluoropolymers, etc.

An inverted or opposing cone for reflecting the axial remnants from cone-tipped fibers is described in U.S. Pat. Appl. Pub. No. 2009/0240242 (Neuberger) along with a reprise of '320 and '308 where grooves are formed within the diameter of the fiber to produce a leakage pattern, a reprise of '347 where a hollow cone is machined in the end of an orb-tipped fiber, and combinations of hollow cones as well as auxiliary conical reflectors and simple axial output fibers protected by capsules or sleeves.

Generally addressing the deficiencies of cone-tipped optical fibers used in ELA treatment of varicose veins, including those housed within protective capsules, '242 teaches the addition of a secondary reflector 112 as depicted in FIG. 11. More completely, an optical fiber having a cladding 100 and a core 104 is equipped with a polished conical tip 110 where the angle of the cone is designed to reflect substantially all of the energy within the fiber core to angles significantly displaced from the fiber longitudinal axis. This does not occur for a simple cone tip fiber (FIG. 12) for a variety of reasons, one being imperfect cone tips 102 that allow emission of substantially axial radiation that, according to publication '242, will be intercepted and reflected by a second cone 112 made of quartz and sealed within the typical quartz protective capsule 106 found in much of the prior art.

U.S. Pat. Appl. Pub. No. 2010/0179525 (Neuberger) expands upon one embodiment within Pub. No. '242 and adds fiber centering mechanisms much like those disclose within Gowda, et al., and Appling. The single embodiment of Pub. No. '242 that appears to be expanded upon in the addition on FIG. 12 within Pub. No. '525 is not described within the text and is, as such, impossible to analyze. Notwithstanding this caveat, FIG. 12 in Pub. No. '242 appears to be a foreshortened version of one of the embodiments within prior art '097, where the protective cap 76 to FIG. 9 is replaced by a flat window about the chamfered opening 70.

U.S. Pat. Appl. Pub. No. 2011/0282330 (Harschack, et al.) teaches a variation of '320 and '308 where a series of grooves on one side of a fiber, or a spiral groove encircling the fiber, is/are replaced by what amounts to be circumferential grooves, described in Pub. No. '525 as "truncated cones".

U.S. Pat. Appl. Pub. No. 2015/0057648 (Swift, et al.) teaches grooves and patterned grooves in a fiber for causing patterned leakage similar to the grooves in a sleeved and shaped fiber produced in our laboratory two decades ago and taught in U.S. Pat. No. 6,113,589 (Levy, et al.) for endometrial coagulation or ablation.

SUMMARY

One embodiment is a radial emission optical fiber termination (FIG. 15) that includes an optical fiber that includes a fluorine-doped-silica clad, silica core fiber (200) which has a core diameter (201); the optical fiber having an up-tapered terminus (205), the up-tapered terminus having a maximum taper diameter (206) of at least 1.5 times the core diameter, the up-tapered terminus having a length (207) greater than 5 times, 10 times or 15 times the core diameter (201) or in a range of about 3 to about 20 times the core diameter (201); the up-tapered terminus ending at a conical tip (211) which has an apex angle (212) in a range of about 70° to about 90°.

A second embodiment is radial emission optical fiber termination that includes a fiber cap that includes a glass tube and an optical element that bisects the glass tube, the glass tube including an open end adapted to receive an optical fiber and a closed end; the optical element consisting of fused quartz or fused silica and having an input face proximal to the open end of the glass tube and a conical face proximal to the closed end of the glass tube. Preferably, the fiber cap includes a bubble between a closed end surface and the optical element; where, for example, the bubble is a vacuum bubble, or a low-vacuum bubble.

BRIEF DESCRIPTION OF THE FIGURES

For a more complete understanding of the disclosure, reference should be made to the following detailed description and accompanying drawing figures wherein:

FIG. 1 is a side view of prior art '390, an early cone-tipped fiber housed within a transparent protective capsule (cap) to preserve conditions required for refraction of the output of the fiber and shaped to further refract that output.

FIG. 2 is a cross-section view of prior art '877, an axial firing fiber (flat tip) housed within a protective cap designed to shape the output of the fiber.

FIG. 3 is a cross-section of prior art '684, an axial firing fiber like that in FIG. 2 where the transparent protective cap is replaced by a metallic cap equipped with a terminal lens for shaping the output of the fiber.

FIG. 4 is a side view of prior art '320, a lateral output fiber designed to emit light at multiple points near the terminus by increasingly core invasive total internal reflection (TIR) notches and a standard TIR bevel at the terminus.

FIG. 5 is a side view of unpublished prior art designed to correct the deficiencies of the art depicted in FIG. 4.

FIG. 6 is a side view of a conical metallic reflector at the distal terminus of a hollow waveguide, designed to radially emit $CO_2$ laser radiation as described in prior art '239.

FIG. 7 is a cross-section of a silica fiber optic equipped with a metallic cone reflector from prior art '235.

FIG. 8 is a cross-section depicting a conical void output fiber as taught in prior art '347.

FIG. 9 is a cross-section of prior art '097 wherein a solid core fiber to annular core fiber converter is equipped with a chamfer at the annular core opening for total internal reflection, the solid core end spliced to a solid core fiber and the assembly protected with a quartz cap.

FIG. 10 depicts prior art '438 in cross-section where a solid core to annular core fiber converter is butt coupled to a solid core fiber at the solid core end to convert the standard conical output into an annular output for reflection at a distal metallic reflector.

FIG. 11 is a cross-section drawing of prior art '242 where the undesirable forward output of a cone tip fiber is said to reflect at a second cone of quartz fused within a quartz protective cap.

FIG. 15A, FIG. 15B and FIG. 15C are partial cross-sections of an embodiment of the invention illustrating the components of construction (FIG. 15A), the calculated output (FIG. 15B) of the embodiment and a detail (FIG. 15C).

FIG. 16A and FIG. 16B are cross-sections at two scales, with and without calculated output ray traces, of a preferred embodiment of the invention.

FIG. 17A, FIG. 17B and FIG. 17C are cross-sections of a preferred embodiment of the invention with calculated ray trace cartoons (FIG. 17B and FIG. 17C) illustrating the different output patterns in air (FIG. 17B) and in biological fluids (FIG. 17C).

FIG. 18A and FIG. 18B are cross-sections of an embodiment of the invention, with (FIG. 18B) and without (FIG. 18A) superimposed ray traces depicting the calculated output.

FIG. 19A and FIG. 19B are cross-sections of an illustrative embodiment, with (FIG. 19B) and without (FIG. 19A) superimposed ray traces depicting the calculated output.

FIG. 20A and FIG. 20B are cross-sections of a preferred embodiment, with (20B) and without (20A) superimposed ray traces depicting the calculated output.

While specific embodiments are illustrated in the figures, with the understanding that the disclosure is intended to be illustrative, these embodiments are not intended to limit the invention described and illustrated herein.

DETAILED DESCRIPTION

Radial emission or output, as used herein, will be restricted to describing fiber emission that does not contain a significant axial component nor angular component that would normally be present in a flat polished, axial output fiber of like NA when used within a similar environment. True radial emission, as used herein, will refer exclusively to radial emission as described above, that spans 360° about the fiber circumference with divergence that is lower than, equal to or at least does not greatly exceed the divergence from a flat polished, axial output fiber of like NA when used under the same conditions Flat tip fibers, in conjunction with laser generators operating at wavelengths where hemoglobin absorbs strongly, are commonly used in ELA surgeries to heat blood and indirectly coagulate or kill damaged vessel walls in the treatment of varicose veins. Prior art teaches avoiding contact between the fiber tip and the vessel wall for preventing perforations. Alternatively, wavelengths that are not strongly absorbed by hemoglobin have been taught for direct heating of vessel walls using radial emission fibers ranging from simple cone tips housed in quartz caps to myriad more complicated constructions designed to overcome the deficiencies of quartz capped, cone tip fibers. While treated as completely separate approaches within the prior art and marketing materials, in reality there is a considerable component of the former strategy expressed within the later surgery due to less than optimum redirection of fiber output.

Minimization of the indirect heating component within the direct heating technique is a common goal among those familiar with the art. Shorter paths from fiber output to vessel walls are advantageous for minimizing interaction with blood or irrigation fluids with the shortest path being orthogonal to the fiber axis at the output tip. Similarly, efficiency in redirecting the laser light to the vessel wall target is advantageous for requiring less laser energy to be used and minimization of the indirect heating component of the surgery.

The invention disclosed provides orthogonal output at high efficiency through the use of a radial emission component that is attached via adhesive to a simple, flat polished fiber (or fibers in the case of multiple outputs).

Figure 12:
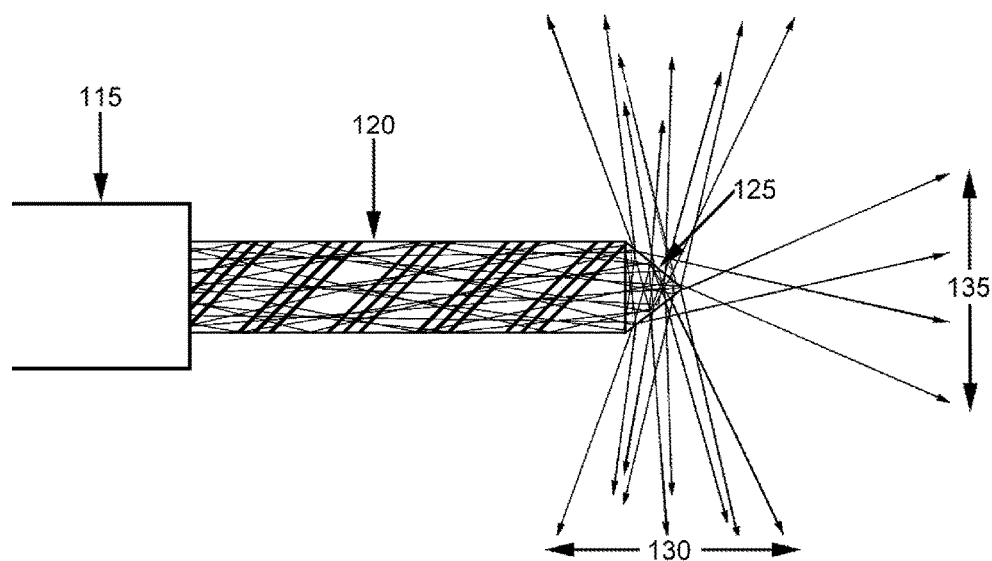
FIG. 12 is a ray trace cartoon illustrating a typical of cone tipped fiber output under the assumption of a defect-free conical surface and essentially infinitely small cone apex.

Early attempts to increase the divergence from fibers for use in ELA treatment of varicose veins included replacing flat tipped fibers with ground and polished cone tip fibers such as that depicted in FIG. 12. The results were disappointing for a variety of reasons. Cone tipped fibers do produce widely diverging outputs, in air, but this characteristic is largely absent in blood and saline irrigation fluids. Refraction and total internal reflection (both are involved in cone tip fiber output) are proportional and dependent upon smooth boundaries between two different refractive indices. The much more closely matching refractive index of blood and irrigation fluids to the fused silica fiber core largely eliminates the effect of cones, lenses, etc. machined upon fiber tips ($\eta_{silica}$=1.46, $\eta_{air}$=1.00, $\eta_{blood}$=1.38 and $\eta_{saline}$=1.34), particularly where cone tips are produced upon lower NA fiber than the flat tip output fibers they were intended to replace.

FIG. 12 is a ray trace cartoon of a 0.22 NA fiber 120 that is denuded of polymer coating 115 near a terminus and the terminal tip is ground and polished to a cone 125. The output off the fiber axis 130 is a function of the fiber NA, the angle of the cone 125 and the refractive indices of the fiber core and medium in which the fiber operates.

At lower angles than shown in FIG. 12, the undesirable output 135 (output of axial character) may be reduced, in theory, as the cone angle is reduced to angles more in keeping with the criterion for total internal reflection (TIR) as defined by Snell's law for the filled fiber NA, but the angle of the radial output (referencing the central ray within the diverging emission, for example the arrow with arrowhead pointing to 130 in FIG. 12) is also directly proportional to the cone angle; the output of the central ray, relative to the longitudinal axis of the fiber, is equivalent to the total included angle of the cone, or apex angle. As opposed to theory, in practice as cone angles are reduced (cones are made physically longer), the amount of the undesirable, axial character output is typically little affected and may actually increase, as the sharper and more delicate points of the longer cones are more difficult to polish to minimal optical quality specifications, e.g. scratch-dig, irregularity, centricity.

Notably, critical angles as classically calculated by Snell's law are relative to the normal to the refractive index interface and, as such, are the complementary angle to the angles referenced herein and within the closely related art for side fire fibers, also known as lateral delivery fibers. Where the critical angle is classically a minimum angle for total internal reflection (TIR), herein critical angles are a maximum.

Similar to side fire fibers, cone tipped fibers also undergo far more complex reflections and refractions that are expected upon cursory review. Excited modes within multimode optical fiber are not all the meridional modes and actual mores are certainly not all $0^{th}$ order meridional modes as depicted in most prior art cartoons illustrating anticipated device function. In fact, for most multimode lasers used in surgery, including the relatively low powered diodes lasers used in ELA, the majority of excited modes in the large core fiber optics of this art are skew modes: modes that do not cross the fiber axis at all. The use of meridional and $0^{th}$ order modes in large core multimode fiber optics design is a gross over-simplification, at best.

Figure 13:
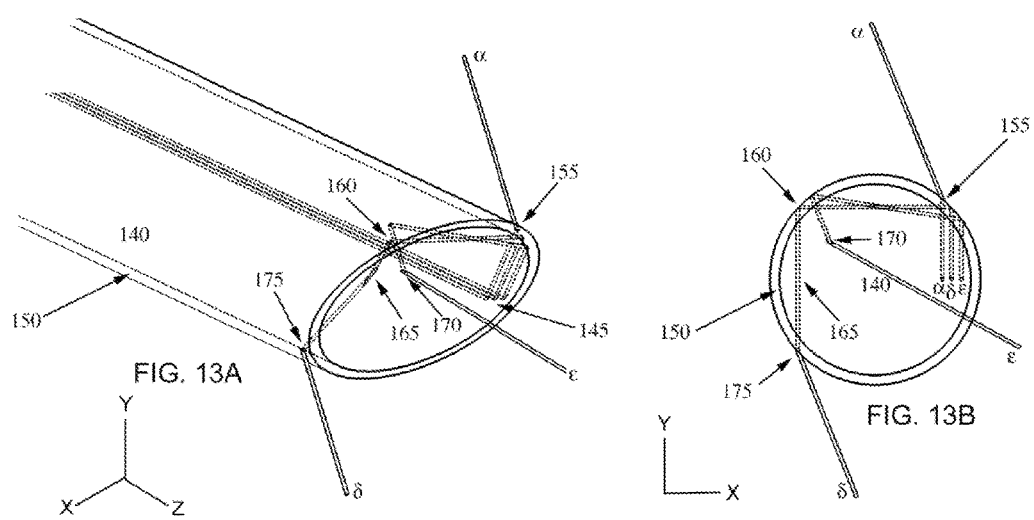
FIG. 13A and FIG. 13B are ray trace cartoons adapted from prior art in illustration of the complexity of reflections within bevel tipped round optical fibers.

Two dimensional ray tracing such as that used to produce FIG. 12 also fails to capture the complexity of light transmission within cone tips and bevel tips for multimode fiber, as illustrated in FIG. 13; two cartoons where three rays ($\alpha$, $\delta$ and $\epsilon$) that are of simple order parallel to the fiber longitudinal axis—are mapped to show their partial fates (Fresnel reflections upon exiting the fiber are not shown) in contacting a typical bevel tipped side fire fiber such as the terminal reflector 34 in FIG. 4. FIG. 13A is an isometric view and FIG. 13B is an end view along the fiber axis. The core 140 and cladding 150 are treated as one, for simplification, because the refraction contribution at the core:cladding interface is a relatively minor perturbation for the purposes of the illustration. Rays $\alpha$, $\delta$ and $\epsilon$ are parallel and encounter the TIR bevel at 145. The innermost ray, $\alpha$, is refracted at the glass:air boundary at 155 because the angle of contact is too high for TIR. The middle ray, $\delta$, imparts the glass:air boundary at an angle that is acute enough to total reflect the ray to the opposite side of the fiber 160 where the contact angle is the same, again reflecting the ray, but now in generally the opposite direction of the intended output. Ray $\delta$ next encounters the TIR face, again, at 165, reflects again and finds the glass:air boundary angle at 175 sufficiently obtuse to exit with refraction. The outermost ray depicted, $\epsilon$, follows a path similar to that taken by $\delta$ but more acute reflections within the fiber tip being it to the TIR bevel glass:air boundary at an angle sufficiently obtuse to escape through the bevel face at 170. Refractions and reflections in cone tips are more complex than this simplified and planar TIR bevel.

In short, the optical model of a cone tip is extremely complex and gives rise to highly distorted emissions, relative to those that are anticipated by oversimplified ray tracings, similar in kind and quantity to those that are known and yet incompletely modeled for side fire fibers. FIG. 13 is an approximation, only, adapted from U.S. Pat. No. 5,428,699 (Pon), where it first appeared in an explanation of the almost 50% reduction in scatter (primarily backscatter) seen in side fire fibers produced upon 1.4 CCDR fiber (Cladding to Core Diameter Ratio) with respect to 1.1 CCDR fiber: the larger total glass (cladding) diameter eliminates the more acute angles of incidence upon the glass:air interface, preventing secondary total internal reflections and reducing the amplitude of Fresnel reflections within the lateral output device. Such a solution is unavailable for cone tipped fibers because the TIR surface is centrosymmetric about the fiber longitudinal axis, thereby removing the very surface essential for application of the art in '699. Furthermore, the curvature of the glass:air interface becomes progressively smaller for cone tipped fibers, exacerbating the undesirable reflection issues briefly taught in '699.

While the addition of a transparent cap about the cone tipped fiber (typically fused quartz) serves to preserve the necessary refractive index difference for wider divergence (or off axis annular output) that is desirable for some approaches in ELA and other surgical interventions, additional refractions and Fresnel reflections at the air to cap interior surface adds additional complexity to the output. Furthermore, in contrast to idealized drawings within prior art, the points of cone tipped fibers are not infinitely small, the walls of the cone are not optically smooth and regular, and the centricity of the cone with respect to the fiber longitudinal axis is relatively poor (most cone tips on fibers are not true right circular cones).

Sub-optimal optical surfaces on cone tipped fibers produce random scattering that reduces the efficiency of treating the targeted vessel wall (or other tissue or disease states) and favors the formation of thromboses about the fiber output. Some chipping is ubiquitous near the apex of mechanically ground and polished cones, and chips produce more concentrated scattering that can produce overtreatment of target tissue, leading to vessel wall perforations. Laser machined cone tips may be made quite smooth and although laser-formed cone walls typically do harbor low amplitude and long period ripples, these imperfections are typically too small to affect more than slight phase shifts in wave fronts that have no real surgical consequences. Laser formed apices and edges are rounded to at least about 50 µm diameter (owing to diffraction limited focus of the laser and heat conduction within the fiber tip), causing leakage that is generally axial and highly divergent that may contribute to formation of a thrombus at the distal terminus of a device, but concentrated errant emission is typically not a problem for laser-formed cone tips.

Where cones narrow from the fiber's glass diameter to a minimum, conical voids (as taught in prior art '347) do offer a constant diameter of curvature for exiting rays in that the exit is through the original fiber outer diameter (cladding) rather than a diminishing cone as is the case in positive cones. Axial leakage remains problematic for conical voids, however, due to the enhanced challenges in their formation as right circular vacancies with smooth wall optical surfaces, and in particular, production of small apices. Machining such concave voids to the very edge of a fiber core is exceedingly difficult on standard CCDR fiber and increasing the CCDR of the fiber is costly in terms of both treasure and the critical dimension of fiber diameter.

Cones produced on annular core fibers are right conical frustum voids (a frustum is a truncated cone or pyramid)—more easily envisioned and referred to by adopting the drafting term of "chamfer"—and, lacking an apex, there is no need to attempt forming one with minimal rounding. Smooth walls are easily produced with laser machining, even for bores in tubes as small as approximately 50 µm, and the angle of the chamfer may be precisely controlled over a very wide range. Although some low amplitude and long period ripple does typically remain, the surfaces produced are highly reflective at the critical angle. A limitation of laser machining is that the bore must be open during the process such that gas flow may be used to prevent silica vapors from depositing within the bore beyond the chamfer. Two dimensional limitations also exist: the bore diameter needs to be larger than the diffraction limited focus of the laser, in general, and the chamfer cannot extend to the outer diameter of the tube. Laser produced chamfers are an easily automated and highly reproducible process for forming reflective surfaces.

It is a thesis of this disclosure that prior art strategies for blocking leaks of light from fundamentally flawed designs yield suboptimal results that are common to treatments that do not address a problem's source. For conversion of a circular solid cross-section beam (solid core fiber) to a hollow core fiber (annular cross-section beam)—an essential element for conical void and chamfer surface reflectors—formation of the apex is a vexing problem for the former but is absent in the latter. For example, the chamfer on the solid core to annular core converter segment depicted in FIG. 9 (from the fusion splice at 68 to the distal terminus at the chamfer 70) is produced on a straight tube under internal gas purge. The tube then is melted and drawn so as to collapse the bore in a controlled manner until it closes (as described in U.S. Pat. No. 5,512,078). The tapered bore is produced at a low angle relative to the longitudinal axis of the tube so as to minimally affect the NA within the converter, and the closure of the bore produces an apex that, while perhaps not infinitely small, is smaller than a wavelength of light typically used in surgery and therefore does not scatter any perceptible amount of light.

Reflective and refractive distortions of the desired output, similar to those in side fire fibers FIG. 13, are still a problem with the annular converter solution disclosed in '097 and the fact that the chamfer TIR surface cannot extend to the edge of the glass diameter produces axial emissions that are quite similar to those seen for cone tipped fibers. $CO_2$ laser ablation can machine chamfers to within approximately 200 µm from the outer edge of a tube 75 without much difficulty, and with great care (and extraordinary process time) the TIR surfaces may extend to within about 100 µm from the edge of the glass before conduction and melt surface tension dominates, joining the outer and inner surfaces in a meniscus. The drawings produced within prior art '097 reflect this issue quite clearly.

Another practical problem is that the cladding on the tube cannot be thicker than approximately 10 µm without adversely affecting the fusion splice at the solid core to annular converter junction. The core of the solid fiber should be larger than the core of the annular converter at the junction to avoid excitation of "cladding modes", or rays confined by the cladding:air interface rather than the core:cladding interface. Any modes capable of exiting the annular core within the non-chamfered annulus of cladding will emit with a generally axial orientation. If it is removed prior to fusion splicing, thicker cladding may be used on the annular converter segment, but this strategy further increase costs of both raw materials and processing. In short, addressing the axial emissions due to incomplete chamfer diameters causes problems in fusion splicing (or otherwise coupling) and device costs rapidly increase.

Notwithstanding cost issues, dimensional constraints obviate the art taught in '097 for ELA and more dimensionally restrictive surgical applications. In FIG. 9, the end of the fiber 72 that conducts energy from the laser to the annular converter segment is depicted as a standard, flat polished tip, but this is not truly the case for embodiments depicted in the original patent. The conducting fiber must be up-tapered prior to joining with the annular converter because the converter both demotes propagated modes to lower angles at the outer diameter and promotes modes to higher angles of propagation at the inner diameter, where the inner diameter is dominant. Without first demoting the highest order modes within the up-tapered fiber segment, some mode angles presenting within the converter segment will not be contained. The length of bare, fragile glass that must be protected by the transparent quartz cap is exceedingly long with the addition of a fiber taper and the total diameter of the device within the cap is several times larger than the base fiber diameter, exceeding dimensional constraints for even the most liberal of surgical applications.

For the balance of the discussion of the invention disclosed, the term "positive cone" and "negative cone" will serve to simplify descriptions of the various embodiments. Feature 125 in FIG. 12 and feature 110 in FIG. 11 are examples of positive cones where 52 in FIGS. 8 and 70 in FIG. 9 represent negative cones. The "special beam splitter" 78 of FIG. 10 is neither a negative or positive cone in that its purpose is merely in support of subsequent redirection of the laser energy, much as is 64 in FIG. 9. Many of the embodiments disclosed will involve fusion of negative cone output surfaces to the inside diameters of protective caps for greatly reducing or eliminating the undesirable scattering that plagues lateral emission devices of all kinds, as depicted in FIG. 13, without suffering the adverse consequences regularly encountered in solutions involving on-fiber fusion (as discussed in U.S. patent application Ser. No. 14/578,739, filed 22 Dec. 2014, the disclosure of which is incorporated herein in its entirety).

Figure 14A:
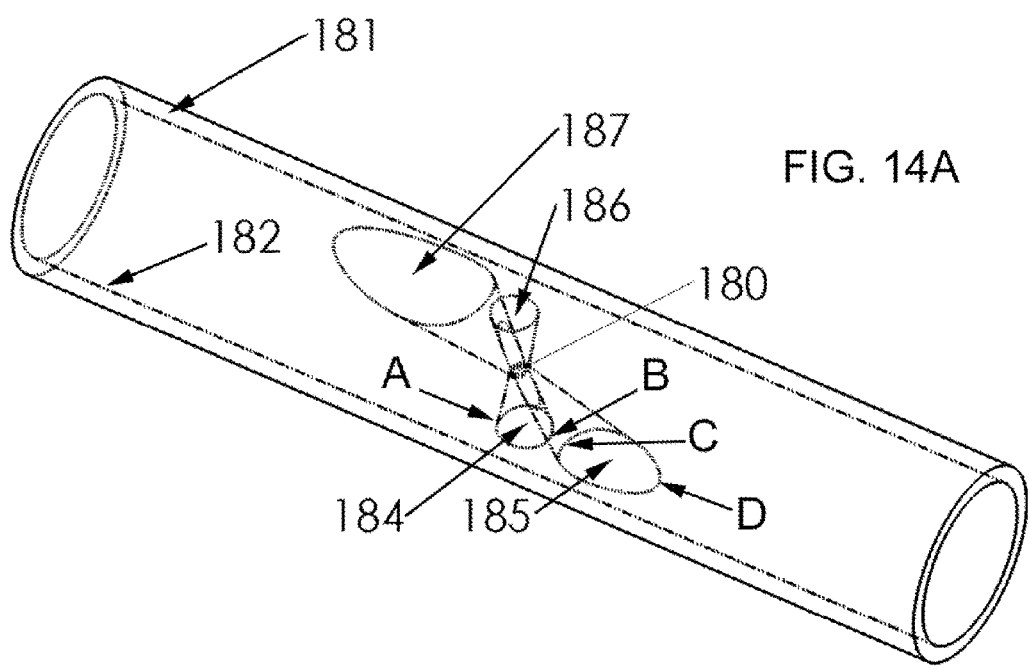
FIG. 14A and FIG. 14B depict the spot sizes of fibers with varying output angle and divergence (FIG. 14A) and plot the energy distribution (FIG. 14B) within two of those spots.

Improvements to performance in radial fiber designs are not limited to the elimination of sources of disorganized and organized scattering, although this is an ultimate goal. FIG. 14 illustrates the importance of divergence and the angle of emission to irradiance from circumferential or radial emission fiber assemblies. In FIG. 14A, four beams are offered for comparison using a side fire (single source) emission for clarity, where emitted beams are normalized to an initial 1 mm diameter. The beams terminate on the "varicose vein" inner wall 182. Beams 184 and 186 deliver the central rays at 90 degrees to the vessel 181 axis where beams 185 and 187 are centered on 45 degrees.

Figure 14B:
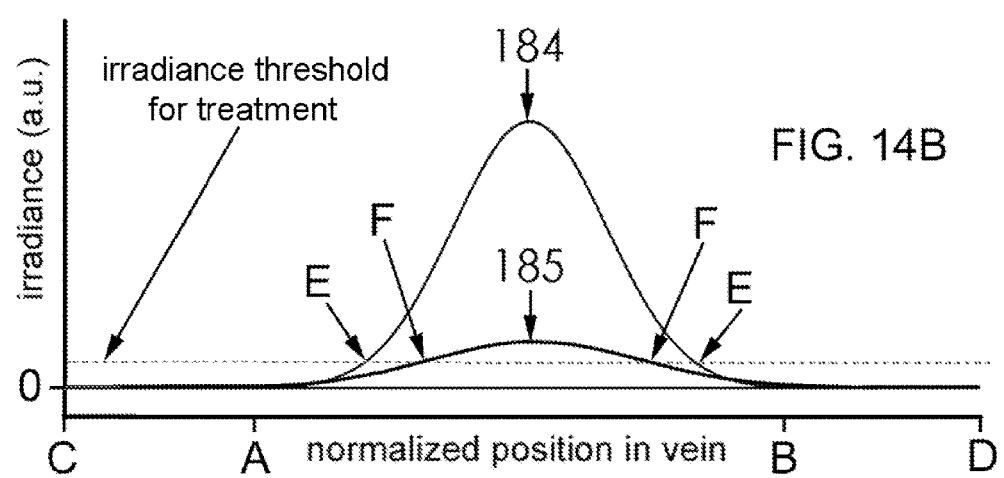
Figure 21A:
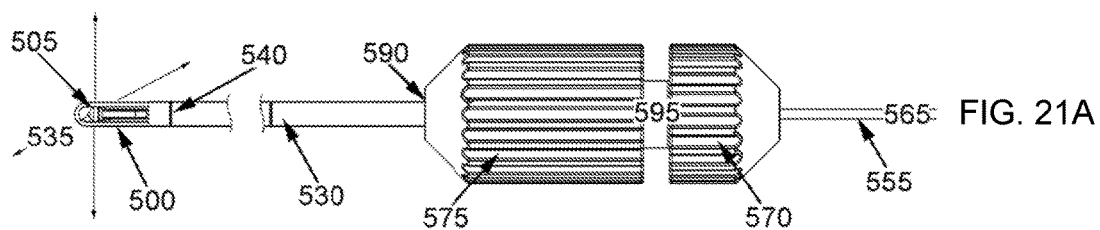
FIG. 21A depicts a resposable embodiment of the invention where
Figure 21B:
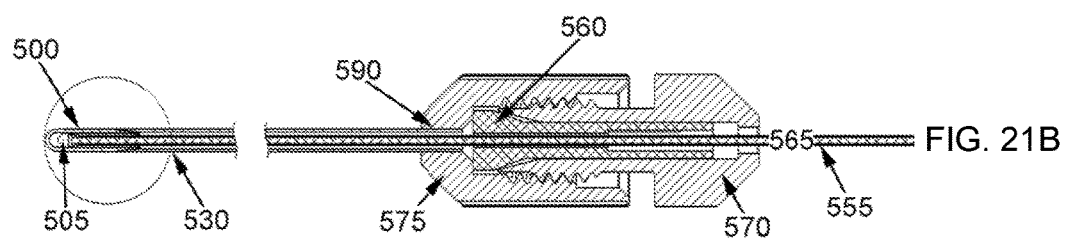
FIG. 21B is the same view in cross-section.
Figure 21C:
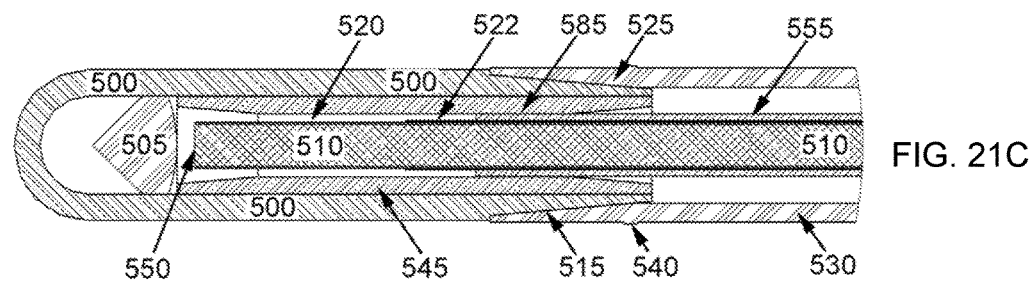
FIG. 21C is a detailed view of the working tip of the device in cross-section and FIG. 21D is an isometric view.
Figure 21D:
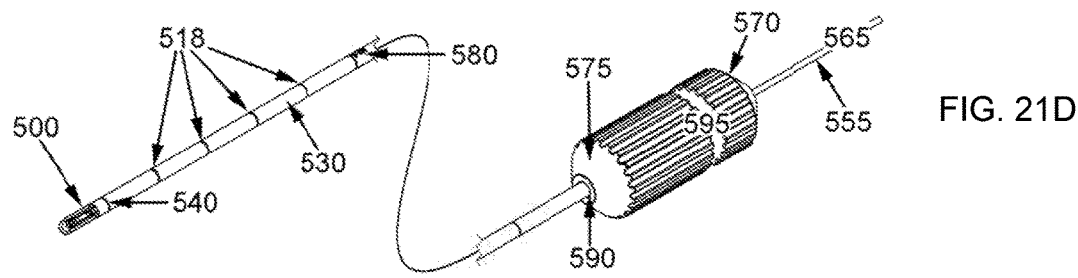

Comparing beams producing spots 184 and 185 illustrates the effect of emission angle, only, upon irradiance: both beams diverge to the same degree. Treatment area 184 is 8.12 $mm^2$ where treatment area 185 is 2.5-fold larger at 20.14 $mm^2$; irradiance is reduced 2.5-fold at 45 degrees versus 90 degrees FIG. 14B is a heuristic plot illustrating the flattening of the beam profile in area 185 with respect to area 184. Points A, B, C and D are provided for referencing positions between FIG. 14A and FIG. 14B. The irradiance plots are relative, not absolute, but server to demonstrate that the diameter E-E of the orthogonal treatment beam 184 is actually larger than the diameter F-F of the more acute angle beam 185, contrary to first impressions, because attenuation and spatial dilution of the acute angle beam reduces much of the irradiance to sub-therapeutic levels (dashed line).

Returning to FIG. 14A, beams producing spots 186 and 187 offer differences in divergence to the mix, where the beam producing 187 diverges twice as much as the beam producing 186. The combined effect of doubling the divergence and reducing the delivery angle to 45 degrees (versus the optimum 90 degrees) results in treatment areas of 5.91 $mm^2$ for area 186 and 46.46 $mm^2$ for area 187: an 8-fold increase in area for an 8-fold reduction in irradiance. A great deal of the laser energy within the beam producing area 187 is lost to absorption in blood, even for laser wavelength within the so-called "therapeutic window", variously defined as spectral regions as wide as 600 nm to 1300 nm and as narrow as 700 nm to 900 nm, where blood and water have absorption minima (also referred to as the "optical window", the "near IR window" and the "biological window").

One embodiment for reducing axial leakage from laser-formed positive cones is depicted in FIG. 15. Therein, a fluorine-doped silica clad, silica core fiber 200 is tapered to approximately twice its original diameter forming an up-tapered terminus 205 over a length of a few millimeters (e.g., about 5 mm in the figure). The up-tapered terminus can have a length 207 that is about 3, 4, 5, 10, 15, or 20 times the core diameter 201; or a length 207 in a range of about 3 to about 20 times the core diameter 201. In some instances, the up-tapered terminus length 207 can be about 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, or 20 mm. The end of up-tapered terminus 205 is laser machined to a cone-tip 211 with an apex angle 212 of approximately 90 degrees. In one instance, the apex angle is in a range of about 70° to about 115°, about 70° to about 110°, about 70° to about 105°, about 70 to about 104°, about 70 to about 100°, about 75° to about 104°, about 75° to about 100°, about 80° to about 104°, about 80° to about 100°, about 85° to about 104°, or about 85° to about 100°. Notably, the term "apex angle" refers to the maximum angle within a cone apex. Geometrically, the apex angle can range from about 1° to about 179°. In a positive cone the apex angle is "within" the substrate forming a cone whereas in a negative cone the apex angle is "outside" of the substrate forming a cone (e.g., in the space about the substrate).

Higher angle modes of laser energy within the fiber 200 are converted to lower angle modes within the up-tapered terminus 205 such that the vast majority of rays imparting the cone wall 220 are totally reflected to the opposing wall where the angle of incidence is such that the rays exit in the desired direction 235. In up-tapering the fiber the cladding at the now larger terminus is about twice as thick. Preferably, the up-tapered terminus 205 has a maximum taper diameter 206 that is at least 1.5 times the fluorine-doped silica clad, silica core fiber 200 core diameter 201, more preferably about 1.5, 1.6, 1.7, 1.8, 1.9, 2.0, 2.1, 2.2, 2.3, 2.4, 2.5, 2.6, 2.7, 2.8, 2.9, or 3 times the core diameter 201. As such, the rounding of the edge 210 does not leak significantly because rounding is contained primarily within the cladding. The rounded apex 215 does leak energy in a generally axial direction 240, but the amount of light lost due to the rounding is approximately one fourth the amount lost for a similar tip formed on the base fiber, without tapering (as a function of the reduction in the fraction of the cross-sectional area of the output occupied by the rounded apex).

In one example, as depicted in FIG. 15A, the radial emission optical fiber termination can be formed from 400 µm core, 1.1 CCDR fiber and fitted with a 0.9 mm bore cap 225 having an outer diameter of 1.6 mm and a length of just over 1 cm: a size well within the dimensional requirements for ELA applications. The protective cap inner diameter conveniently accepts the nylon fiber buffer 230. When affixed, for example with an appropriate medical grade adhesive, the bond between nylon and fused quartz is exceptionally strong and reliable. FIG. 15B illustrates the radial output of the device (modeled in air), an output that is almost orthogonal to the fiber axis and of reduced divergence with respect to the unmodified fiber 200 where equipped with a flat polished tip (neglecting refraction at the cap surfaces). In practice, Fresnel reflections at the inner cap surface contribute to considerable scatter within the output exceeding the primary ring depicted Herewith, this radial emission optical fiber termination can be adapted for use in coronary and cerebral arteries by, for example, employing core fiber with a smaller core diameter and including a lower ratio up-taper.

A second embodiment of a radial emission optical fiber termination is depicted in FIG. 16A. The depiction in FIG.

16 is similar to that in FIG. 15 but, preferably, offers a measure of improved performance within similar or smaller dimensions and affords superior cap retention for enhanced safety in arterial applications. The radial emission optical fiber termination, preferably, includes a fiber cap 275 that includes a glass tube 275 and an optical element 260 that bisects the glass tube. The glass tube 275 can include an open end adapted to receive an optical fiber 250 and a closed end. The optical element 260, preferably consists of fused quartz or fused silica, and has an input face 270 proximal to the open end of the glass tube and a conical face 265 proximal to the closed end of the glass tube.

The input face 270 can include a flat face, a convex lens, a concave lens, an annular lens, or a combination thereof. In one instance, the input face 270 is a convex lens. In another instance (e.g., FIG. 18), the input face 350 is a concave lens.

The optical element 260 has a diameter that is the same as the internal diameter of the glass tube, for example, about 0.1 mm to about 10 mm, about 1 mm to about 4 mm, or about 1.5 mm to about 3 mm. That is, the optical element is fused to an internal wall of the glass tube, preferably wherein the optical element and the glass tube are fused and are a single-unitary piece of fused quartz or fused silica. The optical element 260 has a length from an input face 270 to a cone apex 285 that is about 1, 2, 3, 4, or 5 mm. Preferably, the optical element length is less than 5, 4, or 3 mm.

In one instance, the conical face 265 is a positive cone element formed from large diameter (roughly 0.9 mm), drawn silica rod, and the conical face 265 includes an almost perfect right circular cone. The positive cone element includes a cone-tip 285 with an apex angle of approximately 90 degrees. In another instance, the apex angle is in a range of about 70° to about 115°, about 70° to about 110°, about 70° to about 105°, about 70 to about 104°, about 70 to about 100°, about 75° to about 104°, about 75° to about 100°, about 80° to about 104°, about 80° to about 100°, about 85° to about 104°, or about 85° to about 100°.

The conical face 265, preferably, further includes very smooth surfaces as opposed to those produced upon the ends of far less true rotating and tapered fibers, particularly where cones are formed by mechanical grinding and polishing. (Fiber is chucked upon the buffer to minimize the length of bare glass such that the relatively high buffer eccentricity is limiting for the formation of centrosymmetric cones.) Although the apex 285 remains rounded, better centricity produces a smaller apex than that upon the device in FIG. 15 such that the undesirable axial emissions 245 are further reduced.

The radial emission optical fiber termination can further include an optical fiber, preferably a silica core fiber 250. The optical fiber can include a polymer clad portion and a silica core. Preferably, the optical fiber includes an output positioned within the open end of the glass tube and proximal to the input face of the optical element. In one instance, the silica core fiber 250 includes an up-tapered terminus 255. Herein the up-tapered terminus, 255 (e.g., formed upon the standard 1.1 CCDR fiber 250) while similar to that used in the previous embodiment, can include a shorter length 290. In one instance, the up-tapered terminus 255 can have a length of about 1.5, 2, 3, 4, 5, 10, or 15 times the core diameter; or a length 290 in a range of about 1.5 to about 15 times the core diameter 201. In some instances, the up-tapered terminus length 207 can be about 1 mm, 2 mm, 3 mm, 4 mm, 5 mm, 6 mm, 7 mm, 8 mm, 9 mm, 10 mm, 11 mm, 12 mm, 13 mm, 14 mm, or 15 mm. The silica core fiber 250 carries a polymer (e.g., nylon) coating or jacket 280 and, preferably, the polymer coating or jacket 280 is affixed to (e.g., adhesively) the internal surface 282 of the glass tube 275.

In one example, the shorter length, up-taper terminus 255 is utilized with a convex lens upon the optical element 260 input surface 270. This combination of up-tapered terminus and convex input provides reduction in overall beam divergence while providing a truly orthogonal output 300, preferably, where the center of the diverging output 300 is at right angles (radially) to the fiber longitudinal axis.

The focusing effect of the lens 270, coupled with a taper diameter that is smaller than the cone diameter, absolutely eliminates any potential for axial emissions due to rounding at the outer edge of the cone 277. Fresnel reflections at the cap wall do remain for this embodiment and new Fresnel reflections occur at the lens input surface 270, but the former largely overlap the desired output (owing to the essentially orthogonal angle) and the latter are very diffuse and propagate proximally about the fiber, away from the surgical treatment area.

The optical element 260 (specifically, the cylindrical portion between the lens 270 and cone 265) is fused within the protective cap 275, sealing a low-vacuum, a high-vacuum and/or biocompatible gas within the sealed space, herein the sealed space can be considered a bubble 258 between the closed end surface and the optical element. As used herein, a low-vacuum bubble has a pressure between about 750 to about 25 torr; a high-vacuum bubble has a pressure less than about 24 torr. Preferably, the pressure within the bubble 258 is less than 700, 600, 500, 400, 300, or 200 torr (i.e., a low-vacuum). In another instance, the bubble 285 includes a gas selected from nitrogen, argon, helium, a fluorocarbon, and a mixture thereof at a pressure of less than 700, 600, 500, 400, 300, or 200 torr (i.e., a low-vacuum and including a biocompatible gas). Preferably, the cap is annealed prior to assembly, reducing the potential for stress fracturing during thermal cycling in surgery. In a particularly preferably instance, the taper 255 is less than 3 mm long 290, the overall length of the protective cap 275 may be reduced to less than 1 cm while continuing to allow for the excellent strength and strain relieving bond between the nylon buffer 280 of the fiber and the inner wall of the cap 275.

In another example, the conical face is a negative cone (see e.g., FIG. 17). The negative cone includes an apex angle, which can be approximately 90 degrees. In another instance, the apex angle is in a range of about 70° to about 115°, about 70° to about 110°, about 70° to about 105°, about 70 to about 104°, about 70 to about 100°, about 75° to about 104°, about 75° to about 100°, about 80° to about 104°, about 80° to about 100°, about 85° to about 104°, or about 85° to about 100°.

The negative cone can be made by micromachining the negative cone into a cylindrical segment of fused quartz or fused silica.

Longer solid cylindrical elements are preferred by nature of machining processes where the contact area between micromachining collets and cylindrical materials is higher, providing superior rotational symmetry. This machining precision consideration must be balanced by optical divergence considerations. Were light within the solid cylindrical element 320 is diverging, lengths must necessarily be shorter to insure the bulk of the fiber output imparts the distal optical surface 345 without overfilling the optical aperture of the optical surface. Where up-tapers 305 and lenses 343, and lenses on tapers (not illustrated) are used, divergence is greatly reduced and some degree of convergence may exist for short distances within the optical element 320, permitting somewhat longer segments to be used. In preserving the cylindrical diameter of the optical element 320, negative cones offer superior conical symmetry over positive cone optical elements such as 260 in FIG. 16A.

Yet another consideration remains, however, limiting the practical length of the cylindrical optical elements: overall device rigid length 295 in FIG. 16A. Longer caps 275 are more susceptible to damage and more difficult to pass through endoscopic working channels. Leverage about a flaw located approximately in the center of the cap length should be minimized, also favoring shorter cap length. Optical, mechanical and endoscopic compatibility considerations limit the length of cylindrical optical elements to a maximum of approximately 5 mm for surgical applications, where non-surgical applications may well permit considerably longer and larger diameter elements to be considered.

As the cone surface 345 (FIG. 17A) cannot be easily maintained to the edge of the cylindrical segment (e.g., due to fragility of the material and thermal distortion), a radial emission optical fiber termination with a negative cone (e.g., FIG. 17) is often larger in diameter than the positive cone version (FIG. 16; visible in the Figures by comparing the gap between the fiber buffer 310 and the cap 315 bore wall in FIG. 17A and the fiber buffer 280 and the cap 275 bore wall in FIG. 16A). The centricity advantage for negative cones is somewhat offset by the fact that precision in maintaining a constant cone angle is far higher for positive cones versus negative cones.

As the diameter of the negative cone is often smaller than the diameter of a positive cone (when the internal diameter of the tube is constant) the emissions from the optical fiber must be correctly reflect off of a smaller target. Accordingly, the ratio of the maximum diameter of the up-tapered termination 305 to the internal diameter of the tube with a negative cone is less than the ratio of the maximum diameter of the up-tapered termination to the internal diameter of a tube with a positive cone. Additionally, the linearity of the cone surface limits the maximum off axis angle output 330 achievable; preferably, the divergence in the output from a radial emission optical fiber termination with a negative cone is higher than that of one with a positive cone and some small amount of axial leakage 355 remains.

As the surface area interaction of the parts during fabrication is greater when manufacturing a negative cone embodiment (e.g., up to around 4-fold longer) than in a positive cone embodiment, the alignment of the axes of the protective cap 315 and the cone 320 is more precise. Alignment precision during fusion affects the symmetry of the optical element within the inner surface of the tube and the fact that light reflected from the surface 345, entering the cap 315 does not traverse a refractive index change eliminates Fresnel reflections that occur in positive cone embodiments. FIG. 17B is included for comparison of the ray tracing of the output to FIG. 16B (both assume operation in air) and FIG. 17C is offered for comparing the output 340 in saline or blood to that in air 330 where all other variables are held constant.

In another example, the convex lens of FIG. 17 can be replaced with a concave lens 350 (FIG. 18). In this example, some additional angular redirection may be accomplished 375 (in whole blood) with divergence similar to that in a positive cone embodiment. The cylindrical element upon which the lens 350 and negative cone 360 are formed is, however, quite short 383 and borders on the limits of manufacturability, but the overall diameter of the device is similar to that of other embodiments. Preferably, the tapered fiber 365 abuts the concave lens surface 350 at the cladding of the taper such that an air gap remains between the silica core of the tapered output 380 and the surface of the concave lens 350. The cylindrical element is fused 370 within the bore of the protective cap 355 and annealed. Some axial emission 385 does remain with this embodiment due to the non-zero area of negative apex 362 rounding.

Conical apices imperfections are a common cause of axial emission. Herein, the axial emissions can be eliminating preventing light from reaching a conical apex. In one example, as provided in FIG. 19, the optical element 400 can include a right circular frustum 410 rather than a complete cone with apex (i.e., a frustoconical cone), in another example the cone retains or includes a rounded apex. Additionally and in this example, the optical element 400 includes a convex lens 430 and the optical element is fused 435 to the tube 420. In this embodiment, the apex geometry is less important because the laser delivery fiber(s) includes an annular fiber termination 405 (e.g., via a solid to annular conversion, an annular fiber coupled to the laser source, or an annular (ring) bundle of several fibers).

As shown in the ray trace in FIG. 19B, the annular fiber removes the conical apex or frustum face from the optical path, and all rays from the annular fiber or annular bundle 405 impart the TIR surface 440 distal from the apex or frustum face. In this instance, divergence remains low and the output has true orthogonal character. Scattering due to reflections at the conical frustum surface 440 and at the cap 420 inner wall remain but are far less problematic because these reflections ultimately exit within or very near to the desired output profile, where the output is orthogonal or near orthogonal.

In another embodiment, apical irregularities in radial emission systems can be eliminated by employing a melt-collapsed optical element. Here, the negative apex of the optical element can be formed from melt collapsing a tube rather than machining as depicted in FIG. 20. Such apices can be produced with very small dimensions, for example, the apex dimensions can be smaller than or less than the wavelength of the laser light used. Where the resulting more acute angle θ conical surface 460 (lower angle than the angle ∝ of the TIR cone 475) is lower than the maximum angle of propagation for the light within the delivery fiber 455, the consequence for use of this tactic is promotion of all modes that encounter the surface 460 to angles that are twice θ higher than they were prior to the encounter; a consequence that may be exploited in smoothing semi-Gaussian profiles to profiles with more top hat character, but requiring a reduction in the maximum reflecting cone 475 angle ∝ for TIR at the same time, typically reducing the potential for designing an orthogonal output.

Notably, two examples can be produced from melt collapsed conical apices: higher angle TIR surfaces that redirect incident rays outside the fiber device, and lower angle surfaces that redirect apical rays toward a radial position, preferably toward a second reflective surface. Preferably, the herein described optical element includes a melt collapsed conical apex with a low apex angle (2Θ) and a machined TIR surface that has an apex angle (2∝) as provided in the above embodiments. Herein, the melt-produced or collapsed cone angle 2Θ is, preferably, substantially smaller than the fiber initial internal divergence angle and/or less than, approximately, the arcsine of the numerical aperture divided by the refractive index of the glass assuming the gas or vacuum within the sealed space 478 has a refractive index of approximately 1. That is, the optical element 480, for example as shown in FIG. 20, can include an up-tapered negative cone. As used herein, the up-tapered negative cone includes two conical surfaces which are distinguished by different cone angles or apex angles. By way of distinction, the up-tapered negative cone includes a melt collapsed conical apex 465 that has an up-tapered apex angle (2Θ) that is less than about 10°, preferably less than 9°, 8°, 7°, 6°, or 5°. The up-tapered negative cone further includes a TIR cone that has a TIR apex angle (2∝), notably the precise apical point of the TIR cone is within the negative space of the up-tapered negative cone. The TIR apex angle is in a range of about 70° to about 115°, about 70° to about 110°, about 70° to about 105°, about 70 to about 104°, about 70 to about 100°, about 75° to about 104°, about 75° to about 100°, about 80° to about 104°, about 80° to about 100°, about 85° to about 104°, or about 85° to about 100°.

As shown in FIG. 20A, the optical fiber termination can prevent axial emission by employing an up-tapered conical solid to annular beam converter 460. The optical element 480, preferably, includes an apical point 465 that has a smaller diameter than a wavelength of surgical light, for example, the apical point, preferably, has a diameter of less than 800 nm, 750 nm, 700 nm, 650 nm, 600 nm, 550 nm, 500 nm, 400 nm, 350 nm, 300 nm, or 250 nm. The optical element 480 further includes a TIR conical surface 475, for example machined into a melt collapsed tube pursuant to the description provided in reference to FIG. 17. The optical element 480, preferably consisting of fused quartz or fused silica, and having an input face 470 proximal to the open end of the glass tube 490 and the conical faces 460 & 475 proximal to the closed end of the glass tube 490. The input face 470 can include a flat face, a convex lens, a concave lens, an annular lens, or a combination thereof. Preferably, the input face 470 is a convex lens. Herein, the optical element 480 is fused 485 to the tube 490 yielding a one piece unitary construction that, preferably, consists of fused quartz or fused silica.

The radial emission optical fiber termination can further include a silica core fiber 455. The silica core fiber 455 carries a polymer (e.g., nylon) jacket or coating and, preferably, the polymer jacket or coating is affixed to (e.g., adhesively) the internal surface of the glass tube 490. In one instance, the silica core fiber 455 includes an up-tapered terminus.

In FIG. 20B the radial emission 495 displays similar divergence to the delivery fiber 455 and has orthogonal character. Scatter is greatly reduced due to the fusion 485 of the cylindrical optical element 480 within the cap 490 and any scatter that remains due to imperfections in the fusion region 485 largely overlaps the intended output. Notably in this embodiment, this embodiment eliminates axial emissions and redirects all incident light as axial emissions.

FIG. 21 depicts a resposable embodiment of the invention, where "resposable" means a device within which a component or components, such as a surgical tip or patient contact assembly, is optionally disposable and in which one or more other components, such as a transmitting fiber optic conduit for use with the optionally disposable part, is reusable. A transmitting optical fiber 565, herein a polyamide or polyamide-imide (e.g. nylon) buffered 555, fluoropolymer coated 522, fluorine-doped silica clad 520 and silica core optical fiber 510, has a prepared output tip 550 that is protected by a centering sleeve 545 made of glass, ceramic or metal, disposed about the fiber outer diameter and attached 585 with adhesive or crimping to the fiber buffer 555. Other mechanisms for protecting the transmitting fiber tip 550 will be apparent to those skilled in the art. Preferably, the fiber and centering sleeve are not attached to the fiber cap 500 containing the radial emission optical element 505. In one instance, the fiber cap is chamfered 515 to mate with a matching chamfer 525 within a cannula 530, preferably a semi-rigid cannula. In another instance, the fiber cap 500 is hermetically attached (e.g., adhesively) to the cannula 530.

The semi-rigid cannula 530 can be attached 590 by means of adhesive, solvent welding or other method to a cannula-mount segment 575 of a fiber control device (e.g., a pin vise) 595 having components made of rigid polymer or metal. Accordingly, the fiber cap 500, cannula 530 and cannula-mount segment 575 form a detachable subassembly that includes the entirety of patient contacting components. Notably, the fiber control device 595 includes at least two separable components: a cannula-mount segment 575 and a fiber-holding segment 570. In one instance, the cannula-mount segment 575 and the fiber-holding segment 570 are reversibly affixed by, for example, matching screw threading. Additional reversibly means of affixing the cannula-mount segment 575 and the fiber-holding segment 570 include snap closures, pin-vise connections, a bayonet mount, a BNC-style connector, a RF connector, a UHF connector, a SMA connector, a SMB connector, a SMC connector, a TNC connector, a N connector, a C connector, or the like. The laser connector (not depicted), transmitting fiber optic conduit 565 and the fiber-holding segment 570 (which can include a fiber retaining collet 560) represent a second subassembly comprised of components that are not in patient contact and represent approximately 80% of the device cost.

As a placement aid to use in surgery, the cannula 530 is marked with clearly visible bands spaced one centimeter apart 518, where the first mark 540 is positioned one centimeter proximal to the radial output 535 indicated by the small arrows. Additional markings 580 provide a guide to the depth of insertion; in this case the marking 580 reads "5 cm". By loosening the fiber control device 595, the cap 500, cannula 530 and the cannula-mount segment 575 may be discarded and replaced intraoperatively, greatly reducing the cost of disposable material.

Although the present invention has been described with reference to preferred embodiments, workers skilled in the art will recognize that changes may be made in form and detail without departing from the spirit and scope of the invention.

What is claimed:

1. A radial emission optical fiber termination comprising:
   a fiber cap that includes a glass tube and an optical element that bisects the glass tube,
   the glass tube including an open end adapted to receive an optical fiber and a closed end;
   the optical element consisting of fused quartz or fused silica and having an input face proximal to the open end of the glass tube and a conical face proximal to the closed end of the glass tube, the input face is selected from the group consisting of a convex lens and a concave lens.

2. The optical fiber termination of claim 1, wherein the fiber cap further includes a bubble between a closed end surface and the optical element; wherein the bubble is a low-vacuum bubble.

3. The optical fiber termination of claim 1, wherein the optical element has a diameter that is the same as an inside diameter of the glass tube and has a length that is about 0.1 mm to about 10 mm.

4. The optical fiber termination of claim 1, wherein the conical face is selected from the group consisting of a negative cone and a positive cone.

5. The optical fiber termination of claim 4, wherein the conical face is selected from the group consisting of a negative cone having an apex angle in the range of about 70° to about 100° and a positive cone having an apex angle in the range of about 70° to about 100°.

6. The optical fiber termination of claim 4, wherein the conical face is positive frustoconical.

7. The optical fiber termination of claim 4, wherein the conical face is an up-tapered negative cone; wherein the up-tapered negative cone includes a TIR apex angle in the range of about 70° to about 115° and an up-tapered apex angle of less than 10°.

8. The optical fiber termination of claim 1, wherein the glass tube and the optical element consist of the same material and are a single, unitary piece.

9. The optical fiber termination of claim 1 further comprising an optical fiber that includes a polymer clad portion and a silica core, the optical fiber having an output positioned within the open end of the glass tube and proximal to the input face of the optical element.

10. The optical fiber termination of claim 9, wherein the optical fiber includes an up-tapered termination.

11. The optical fiber termination of claim 9, wherein the optical fiber includes an annular fiber termination.

12. The optical fiber termination of claim 1, wherein the fiber cap is affixed to a cannula.

13. The optical fiber termination of claim 12; wherein fiber cap includes a chamfer; wherein the cannula includes a fiber-cap matching chamfer; and wherein the cannula is adhesively affixed to the cannula about the chamfer and the fiber-cap matching chamfer.

14. The optical fiber termination of claim 12, wherein the cannula is affixed to a cannula-mount segment of a fiber control device.

15. The optical fiber termination of claim 14 further comprising an optical fiber, the optical fiber affixed to a fiber-holding segment of the fiber control device.

16. The optical fiber termination of claim 15 further comprising a centering sleeve disposed about the optical fiber; wherein the optical fiber includes an output tip proximal to the input face of the optical element; and wherein the centering sleeve is disposed about the output tip.

* * * * *